United States Patent
Verma et al.

(10) Patent No.: US 10,881,321 B2
(45) Date of Patent: Jan. 5, 2021

(54) AUTOMATIC TRACT EXTRACTION VIA ATLAS BASED ADAPTIVE CONNECTIVITY-BASED CLUSTERING

(71) Applicant: The Trustees of the University of Pennsylvania, Philadelphia, PA (US)

(72) Inventors: Ragini Verma, Philadelphia, PA (US); Birkan Tunc, Philadelphia, PA (US)

(73) Assignee: The Trustees of the University of Pennsylvania, Blue Bell, PA (US)

( * ) Notice: Subject to any disclaimer, the term of this patent is extended or adjusted under 35 U.S.C. 154(b) by 792 days.

(21) Appl. No.: 15/229,594

(22) Filed: Aug. 5, 2016

(65) Prior Publication Data

US 2017/0035320 A1 Feb. 9, 2017

Related U.S. Application Data

(60) Provisional application No. 62/202,329, filed on Aug. 7, 2015.

(51) Int. Cl.
| | | |
|---|---|---|
| *A61B 5/00* | (2006.01) | |
| *A61B 5/055* | (2006.01) | |
| *G01R 33/563* | (2006.01) | |

(52) U.S. Cl.
CPC ............ *A61B 5/055* (2013.01); *A61B 5/0042* (2013.01); *G01R 33/56341* (2013.01); *G06T 2207/10092* (2013.01); *G06T 2207/30016* (2013.01)

(58) Field of Classification Search
CPC combination set(s) only.
See application file for complete search history.

(56) References Cited

U.S. PATENT DOCUMENTS 8,076,937 B2    12/2011    Holthuizen et al.

OTHER PUBLICATIONS

Roca et al. ("Inter-subject connectivity-based parcellation of a patch of cerebral cortex", Med Image Computer Assist Intervation, 13(PT2)pp. 347-354, 2010.*
O'donnell et al. "Fiber clustering versus the parcellation based connectome" Neuroimage 80 pp. 283-289, 2010.*

(Continued)

*Primary Examiner* — Joseph M Santos Rodriguez
(74) *Attorney, Agent, or Firm* — Howson and Howson LLP; Cathy Kodroff

(57) ABSTRACT

Method and apparatus for processing diffusion data for identification of white matter tracts in the brain of a patient is provided herein. The method involves, with a processor: generating a connectivity based representation of white matter fibers for multiple different subjects from the connectivity signatures of the fibers from a diffusion magnetic resonance imaging (dMRI) without using the physical coordinates of the fibers; generating a fiber bundle atlas from the connectivity based fiber representation of (a) which define a model of the human brain; adaptively clustering fibers of a new patient utilizing the fiber bundle atlas of (b) to extract white matter tracts without manual intervention in the form of drawing regions of interest; and presenting the selected white matter tracts and diffusion data in a report or on a display device. This method and apparatus can be used even for patients having edema or brain perturbations.

13 Claims, 14 Drawing Sheets

(56) References Cited

OTHER PUBLICATIONS

Aarnink, et al. (2014). "Automated longitudinal intra-subject analysis (ALISA) for diffusion MRI tractography." Neuroimage 86: 404-416.(Oct. 2013).
Abdullah, et al. (2013). "Use of diffusion tensor imaging in glioma resection." Neurosurgical focus 34(4): E1. (Apr. 2013).
Ashburner, et al. "Voxel-based morphometry—the methods." *Neuroimage* 11.6 (2000): 805-821. (Jun. 2000).
Basser et al. "Estimation of the effective self-diffusion tensor from the NMR spin echo." *Journal of Magnetic Resonance, Series B* 103.3 (1994): 247-254. (Mar. 1994).
Basser et al."MR diffusion tensor spectroscopy and imaging." *Biophysical journal* 66.1 (1994): 259-267. (Jan. 1994).
Basser, et al. (2000). "In vivo fiber tractography using DT-MRI data." Magnetic resonance in medicine 44(4): 625-632. (Oct. 2000).
Bazin, et al. (2011). "Direct segmentation of the major white matter tracts in diffusion tensor images." Neuroimage 58(2): 458-468. (Epub Jun. 2011).
Behrens, et al. (2007). "Probabilistic diffusion tractography with multiple fibre orientations: What can we gain?" Neuroimage 34(1): 144-155. (Epub Oct. 2006).
Bishop (2006). "Pattern Recognition and Machine Learning (Information Science and Statistics) Springer-Verlag New York." Inc. Secaucus, NJ, USA.
Brem, et al. (2011). "Central nervous system cancers." Journal of the National Comprehensive Cancer Network 9(4): 352-400. (Apr. 2011).
Brun, et al. (2004). "Clustering Fiber Traces Using Normalized Cuts." Med Image Comput Comput Assist Interv 3216/2004(3216): 368-375. (Sep. 2004).
Bujnošková, et al. (2014). "22. Comparison of the methods for brain parcellation." Clinical Neurophysiology 125(5): e31-e32.
Burgel, et al. (2009). "Fiber tracking with distinct software tools results in a clear diversity in anatomical fiber tract portrayal." Central European Neurosurgery 70(01): 27-35. (Epub Feb. 2009).
Chen, et al. (2015). "Reconstruction of the arcuate fasciculus for surgical planning in the setting of peritumoral edema using two-tensor unscented Kalman filter tractography." NeuroImage: Clinical 7: 815-822. (Mar. 2015).
Cook, et al. (2006). Camino: open-source diffusion-MRI reconstruction and processing. 14th scientific meeting of the international society for magnetic resonance in medicine, Seattle WA, USA. In Scientific Meeting of the International Society for Magnetic Resonance in Medicine (p. 2759) (2006).
Cote, et al. "Tractometer: towards validation of tractography pipelines." *Medical image analysis* 17.7 (2013): 844-857. (Apr. 2013).
Craddock, et al. (2013). "Imaging human connectomes at the macroscale." Nature methods 10(6): 524-539. (Jun. 2013).
Dempster et al. Maximum likelihood from incomplete data via the EM algorithm. Journal of the Royal Statistical Society B. 1977;39(1):1-38.
Desikan, et al. (2006). "An automated labeling system for subdividing the human cerebral cortex on MRI scans into gyral based regions of interest." Neuroimage 31(3): 968-980. (Epub Mar. 2006).
Dice (1945). "Measures of the amount of ecologic association between species." Ecology 26(3): 297-302. (Jul. 1945).
Dowson, et al. (1982). "The Frechet distance between multivariate normal distributions." Journal of multivariate analysis 12(3): 450-455. (Sep. 1982).
Eyupoglu, et al. (2013). "Surgical resection of malignant gliomas—role in optimizing patient outcome." Nature Reviews Neurology 9(3): 141-151. (Jan. 2013).
Farquharson, et al. (2013). "White matter fiber tractography: why we need to move beyond DTI: Clinical article." Journal of neurosurgery 118(6): 1367-1377. (Epub Mar. 2013).
Fillard, et al. "Quantitative evaluation of 10 tractography algorithms on a realistic diffusion MR phantom." *Neuroimage* 56.1 (2011): 220-234. (Jan. 2011).
Ge, et al. (2012). "Group-wise consistent fiber clustering based on multimodal connectional and functional profiles." Med Image Comput Comput Assist Interv 15(Pt 3): 485-492.
Golby, et al. (2011). "Interactive diffusion tensor tractography visualization for neurosurgical planning." Neurosurgery 68(2): 496. (Feb. 2011).
Guevara, et al. "Automatic fiber bundle segmentation in massive tractography datasets using a multi-subject bundle atlas." *Neuroimage* 61.4 (2012): 1083-1099. (Mar. 2012).
Guevara, et al. (2011). Segmentation of short association bundles in massive tractography datasets using a multi-subject bundle atlas. Iberoamerican Congress on Pattern Recognition, Springer. In: San Martin C., Kim SW. (eds) Progress in Pattern Recognition, Image Analysis, Computer Vision, and Applications. CIARP 2011. Lecture Notes in Computer Science, vol. 7042. Springer, Berlin, Heidelberg.
Hofer, et al. (2006). "Topography of the human corpus callosum revisited—comprehensive fiber tractography using diffusion tensor magnetic resonance imaging." Neuroimage 32(3): 989-994. (Epub Jul. 2006).
Ito, et al. (2013). "Automatic extraction of the cingulum bundle in diffusion tensor tract-specific analysis: feasibility study in Parkinson's disease with and without dementia." Magn Reson Med Sci 12(3): 201-213. (Jul. 2013).
Jenkinson, et al. (2012). "Fsl." Neuroimage 62(2): 782-790. (Epub Sep. 2011).
Klein, et al. (2012). "101 labeled brain images and a consistent human cortical labeling protocol." Frontiers in neuroscience 6: 171. (Prepublished online Sep. 2012).
Lecoeur, et al. (2014). Addressing the challenge of edema in fiber tracking. MICCAI 2014 DTI Tractography Challenge, Sep. 2014, Boston, United States. 2014.
Lerner, et al. (2014). "Clinical applications of diffusion tensor imaging." World neurosurgery 82(1): 96-109. (Epub Aug. 2013).
Li, et al. (2010). "A hybrid approach to automatic clustering of white matter fibers." Neuroimage 49(2): 1249-1258. (Epub Aug. 2009).
Liu, et al. (2012). "Unsupervised Automatic White Matter Fiber Clustering Using a Gaussian Mixture Model." Proc IEEE Int Symp Biomed Imaging 2012(9): 522-525. (May 2012).
Maddah, et al. (2008). "A unified framework for clustering and quantitative analysis of white matter fiber tracts." Med Image Anal 12(2): 191-202. (Oct. 2007).
Maddah, et al. (2011). "Sheet-like white matter fiber tracts: representation, clustering, and quantitative analysis." Med Image Comput Comput Assist Interv 14(Pt 2): 191-199.
Mazziotta, et al. (2001). "A probabilistic atlas and reference system for the human brain: International Consortium for Brain Mapping (ICBM)." Philosophical Transactions of the Royal Society of London B: Biological Sciences 356(1412): 1293-1322. (Aug. 2001).
Mori, et al. (2002). "Fiber tracking: principles and strategies—a technical review." NMR Biomed 15(7-8): 468-480.(Nov. 2002).
Nazem-Zadeh, et al. (2011). "Atlas-based fiber bundle segmentation using principal diffusion directions and spherical harmonic coefficients." Neuroimage 54 Suppl 1: S146-164. (Available online Sep. 30, 2010).
Nimsky, et al. (2005). "Preoperative and intraoperative diffusion tensor imaging-based fiber tracking in glioma surgery." Neurosurgery 56(1): 130-138. (Jan. 2005).
Nimsky, et al. (2007). "Preoperative and intraoperative diffusion tensor imaging-based fiber tracking in glioma surgery." Neurosurgery 61(1 Suppl): 178-185; discussion 186.
O'Donneli et al. "Automatic tractography segmentation using a high-dimensional white matter atlas." *IEEE transactions on medical imaging* 26.11 (2007): 1562-1575. (Oct. 2007).
O'Donnell, et al. "Tract-based morphometry for white matter group analysis," *Neuroimage* 45.3 (2009): 832-844. (Dec. 2008).
O'Donnell, et al. (2006). "A method for clustering white matter fiber tracts." AJNR Am J Neuroradiol 27(5): 1032-1036. (May 2006).
O'Donnell, et al. (2012). "fMRI-DTI modeling via landmark distance atlases for prediction and detection of fiber tracts." Neuroimage 60(1): 456-470. (Epub Dec. 2011).
O'Donnell, et al. (2013). "Fiber clustering versus the parcellation-based connectome." Neuroimage 80: 283-289. (Apr. 2013).

(56) References Cited

OTHER PUBLICATIONS

Ou, et al. (2011). "DRAMMS: Deformable registration via attribute matching and mutual-saliency weighting." Med Image Anal 15(4): 622-639. (Epub Jul. 2010).

Pieper, et al. (2004). 3D Slicer. Biomedical Imaging: Nano to Macro, 2004. IEEE International Symposium on, IEEE. In: IEEE International Symposium on Biomedical Imaging; p. 632-635.

Pierpaoli, et al. (1996). "Toward a quantitative assessment of diffusion anisotropy." Magnetic resonance in medicine 36(6): 893-906. (Dec. 1996).

Reynolds, et al. (2000). "Speaker verification using adapted Gaussian mixture models." Digital signal processing 10(1-3): 19-41.

Roca, et al. (2010). "Inter-subject connectivity-based parcellation of a patch of cerebral cortex." Medical image computing and computer-assisted intervention—MICCAI 2010: 347-354.

Sanai, et al. (2008). "Glioma extent of resection and its impact on patient outcome." Neurosurgery 62(4): 753-764; discussion 764-766. (Apr. 2008).

Sanai, et al. (2011). "An extent of resection threshold for newly diagnosed glioblastomas: clinical article." Journal of neurosurgery 115(1): 3-8. (Epub Mar. 2011).

Shattuck, et al. (2008). "Construction of a 3D probabilistic atlas of human cortical structures." Neuroimage 39(3): 1064-1080. (Epub Nov. 2007).

Smith, et al. "Tract-based spatial statistics: voxelwise analysis of multi-subject diffusion data." *Neuroimage* 31.4 (2006): 1487-1505. (Apr. 2006).

Snook., et al. "Voxel based versus region of interest analysis in diffusion tensor imaging of neurodevelopment," *Neuroimage* 34.1 (2007): 243-252. (Oct. 2006).

Song, et al, (2005). Highly efficient incremental estimation of Gaussian mixture models for online data stream clustering. Defense and Security, International Society for Optics and Photonics.. In: Priddy, K.L. (ed), Intelligent Computing: Theory and Applications III. vol. 5803, pp. 174-183 (Mar. 2005).

Suarez, et al. (2012). "Automated delineation of white matter fiber tracts with a multiple region-of-interest approach." Neuroimage 59(4): 3690-3700. ( Epub Nov. 2011).

Tournier, et al. "MRtrix: diffusion tractography in crossing fiber regions." International Journal of Imaging Systems and Technology 22.1 (2012): 53-66. (Feb. 2012).

Tournier, et al. (2011). "Diffusion tensor imaging and beyond." Magnetic resonance in medicine 65(6): 1532-1556. (Epub Apr. 2011).

Tuch et al, "High angular resolution diffusion imaging of the human brain." *Proceedings of the 7th Annual Meeting of ISMRM*, Philadelphia. vol. 321. 1999.

Tuch et al. "High angular resolution diffusion imaging reveals intravoxel white matter fiber heterogeneity." *Magnetic resonance in medicine* 48.4 (2002): 577-582. (Sep. 2002).

Tunc, et al. (2013). "Multinomial probabilistic fiber representation for connectivity driven clustering." Inf Process Med Imaging 23: 730-741.

Tzourio-Mazoyer, et al. (2002). "Automated anatomical labeling of activations in SPM using a macroscopic anatomical parcellation of the MNI MRI single-subject brain." Neuroimage 15(1): 273-289. (Jan. 2002).

Visser, et al. (2011). "Partition-based mass clustering of tractography streamlines." Neuroimage 54(1): 303-312. (Epub Jul. 2010).

Voineskos, et al. (2009). "Quantitative examination of a novel clustering method using magnetic resonance diffusion tensor tractography." Neuroimage 45(2): 370-376. (Dec. 2008).

Wakana, et al. 200). "Reproducibility of quantitative tractography methods applied to cerebral hite matter." Neuroimage 36(3): 630-644.(Mar. 2007).

Wang, et al. "Tractography segmentation using a hierarchical Dirichlet processes mixture model," *NeuroImage* 54.1 (2011): 290-302. (Aug. 2010).

Wang, et al. (2007). Diffusion toolkit: a software package for diffusion imaging data processing and tractography. Proc Intl Soc Mag Reson Med, Berlin. In Intl Soc Mag Reson Med; 3720.

Wassermann, et al. "Unsupervised white matter fiber clustering and tract probability map generation: Applications of a Gaussian process framework for white matter fibers." *NeuroImage* 51.1 (2010): 228-241 (Jan. 2010).

White, et al. (2014), "Diffusion-weighted imaging in cancer: physical foundations and applications of restriction spectrum imaging." Cancer research 74(17): 4638-4652. (Sep. 2014).

Wu, et al. (2012). "Feature-based groupwise registration by hierarchical anatomical correspondence detection." Hum Brain Mapp 33(2): 253-271. (Epub Mar. 2011).

Zhang, et al. (2008). "Automated fiber tracking of human brain white matter using diffusion tensor imaging." Neuroimage 42(2): 771-777. ( Epub Apr. 2008).

Zhang, et al. (2010). "Atlas-guided tract reconstruction for automated and comprehensive examination of the white matter anatomy." Neuroimage 52(4): 1289-1301. (May 2010).

Tunc, et al. (2014). "Automated tract extraction via atlas based Adaptive Clustering." Neuroimage 102 Pt 2: 596-607. (Aug. 2014).

Mukherjee, et al. (2001). "Normal brain maturation during childhood: developmental trends characterized with diffusion-tensor MR imaging." Radiology 221(2): 349-358.

Wang, et al. (2010). Hierarchical fiber clustering based on multi-scale neuroanatomical features. Proceedings of the 5th international conference on Medical imaging and augmented reality. Beijing, China, Springer-Verlag: 448-456. (Sep. 2010).

Kuhn (1955). "The Hungarian method for the assignment problem." Naval research logistics quarterly 2(1-2): 83-97, (Mar. 1955).

\* cited by examiner

FIG 1
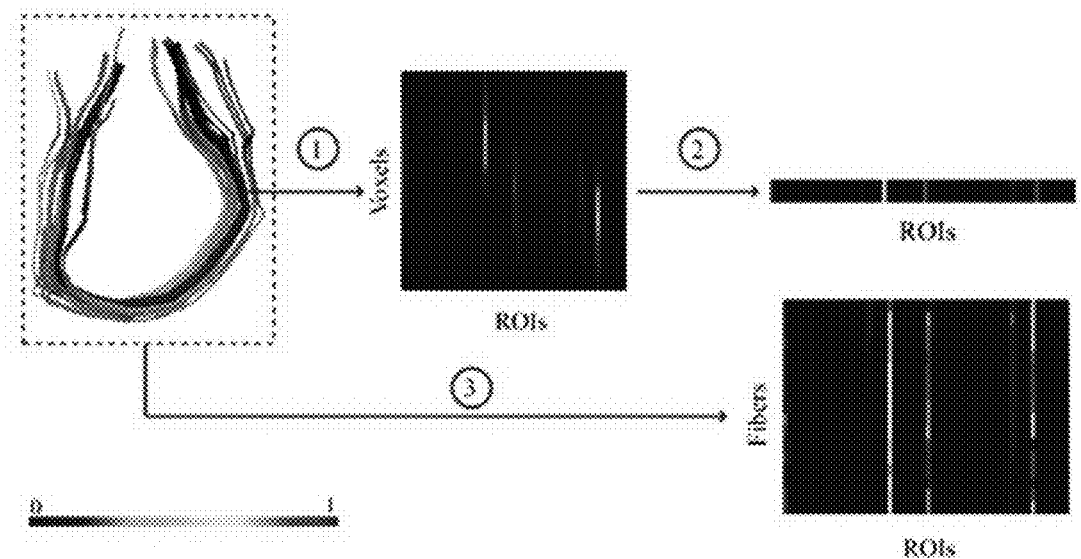
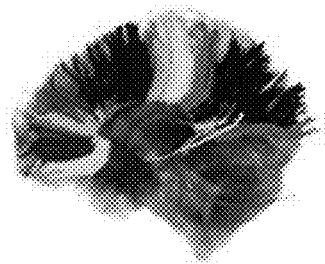
FIG 2A
FIG 2B
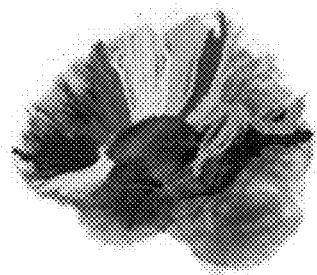
FIG 2C
FIG 2D FIG 7C
<br>
FIG 7F
<br>
FIG 7B
<br>
FIG 7E
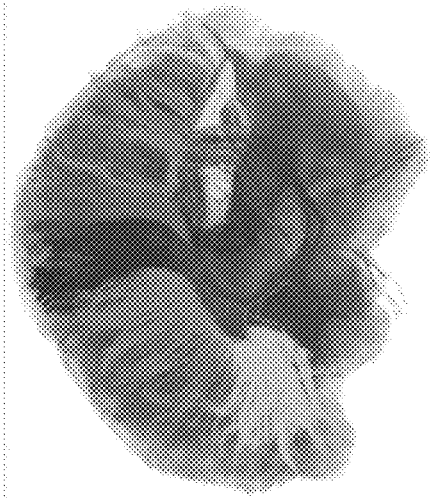<br>
FIG 7A
<br>
FIG 7D

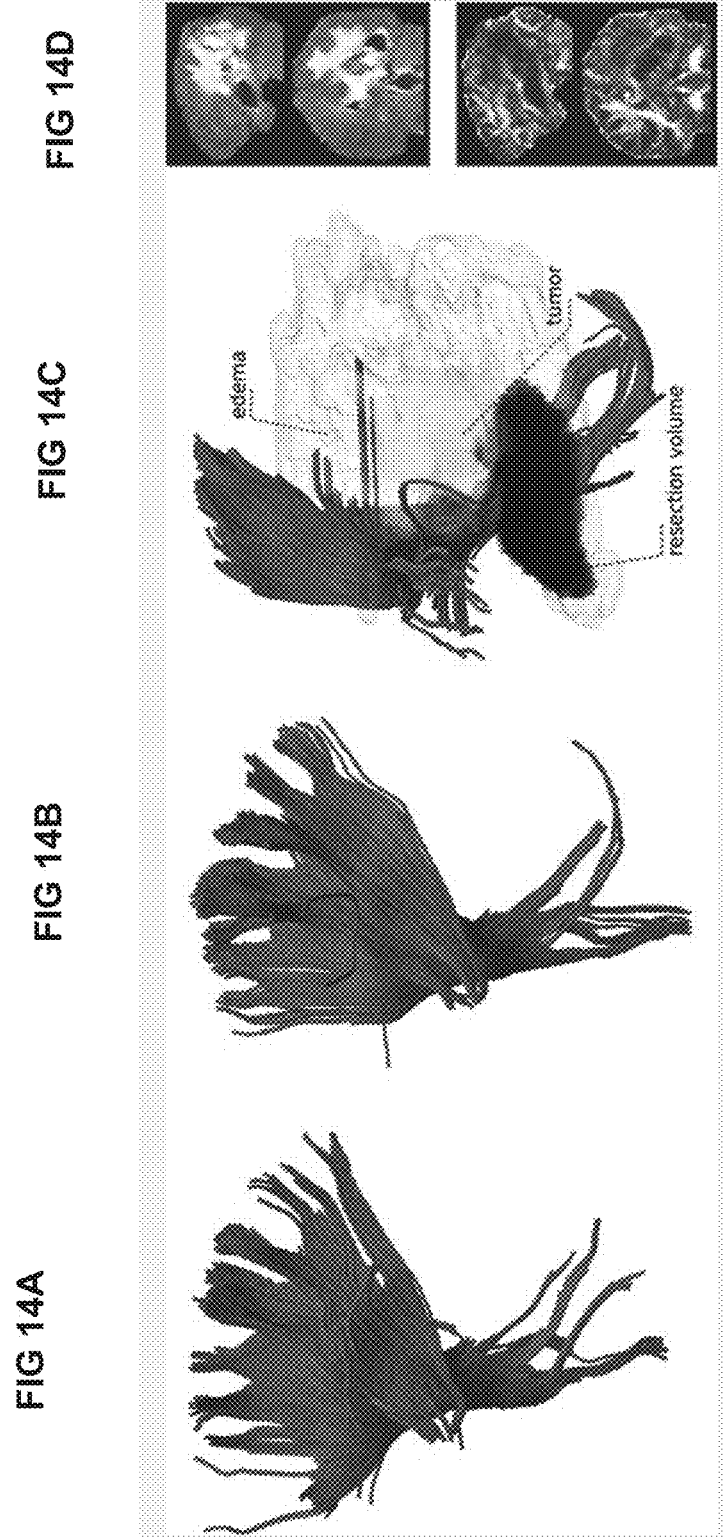

IFOF

ILF

AF

AUTOMATIC TRACT EXTRACTION VIA ATLAS BASED ADAPTIVE CONNECTIVITY-BASED CLUSTERING

CROSS-REFERENCE TO RELATED APPLICATION

This application claims the benefit under 35 USC 1.119(e) of U.S. Provisional Patent Application No. 62/202,329, filed Aug. 7, 2015. This application is hereby incorporated by reference in its entirety.

STATEMENT OF FEDERALLY SPONSORED RESEARCH

This invention was made with government support under grant from grant number R01-MH092862 awarded by the National Institutes of Health. The US government has certain rights in this invention.

BACKGROUND OF THE INVENTION

Due to advancements in the diffusion weighted imaging techniques, white matter (WM) structures in the human brain can now be studied in vivo at a micro-structural level [(Basser et al., (1994a). Journal of Magnetic Resonance. Series B, 103(3), 247-254; Basser, P. J., et al, (1994b). Biophysical Journal, 66, 259-267)]. New imaging protocols such as the high angular resolution diffusion-weighted imaging (HARDI) (Tuch et al., (2002). Magnetic Resonance in Medicine, 48(4), 577-582; Tuch, D. S., et al, (1999). High Angular Resolution Diffusion Imaging of the Human Brain. In Proceedings of the Annual Meeting of ISMRM], based on their superior characterization of the complex WM structure in regions of fiber crossing, have improved the reliability of fiber tractography [(Côté et al., Medical image analysis, 17(7), 844-57 (2013); Fillard et al., NeuroImage, 56(1), 220-34 (2011); Tournier et al., International Journal of Imaging Systems and Technology, 22(1), 53-66 (2012)]. This fact has led to an increasing interest in tract based analyses that have hitherto been performed over traditional (diffusion tensor based) tractography methods (O'Donnell et al., NeuroImage, 45(3), 832-44 (2009); Smith et al., NeuroImage, 31(4), 1487-505 (2006); Snook et al., NeuroImage, 31(4), 1487-505 (2007)]. As an alternative to conventional statistical approaches such as the voxel based morphometry (VBM) (Ashburner & Friston, 2000) and the region based morphometry (RBM) (Mukherjee et al., 2001), statistical analyses over WM tracts can contribute greatly towards the structural analysis of the brain since fiber bundles are the most representative of the connectivity pathways.

The main challenge with tract based studies involving group or longitudinal statistics is the extraction of the tract of interest (TOI) from the whole brain tractography results in a consistent and comparable manner over a large group of individuals. Early works on tract extraction were limited to single subject studies and big, easily discernible WM tracts like the corpus callosum due to the lack of tools that enable extracting TOIs in different individuals automatically without requiring any knowledge of detailed anatomy. Recent research on fiber clustering [(Guevara et al., NeuroImage, 61(4), 1083-99 (2012); O'Donnell & Westin, IEEE transactions on medical imaging, 26(11), 1562-75 (2007); Tunç et al., Multinomial probabilistic fiber representation for connectivity driven clustering. In Information Processing in Medical Imaging (IPMI) (pp. 730-741) (2013); X. Wang et al., NeuroImage, 54(1), 290-302 (2011); Wassermann et al., NeuroImage, 51(1), 228-41 (2010)] has introduced several advancements to facilitate large scale population studies, increasing the applicability of fiber clustering in the real life clinical applications.

The common approaches for tract extraction rely on fiber tractography by using either supervised or unsupervised post processing of the reconstructed fibers. Supervised methods require the placement of inclusion and exclusion ROIs (regions of interest) to extract WM tracts by eliminating the unintended fiber pathways [Mori & van Zijl, Fiber tracking: principles and strategies—a technical review. NMR in biomedicine, 15(7-8), 468-80 (2002); Wakana et al., NeuroImage, 36(3), 630-44 (2007)]. This procedure can be automated by registering different scans of the subjects to a template space [Aarnink et al., NeuroImage, 86, 404-16 (2014)], thereby extracting any TOI simultaneously. Unsupervised methods, on the other hand, utilize fiber-based features within a clustering framework to automatically generate tracts that are characterized inherently by these features [Maddah et al., Medical Image Computing and Computer-Assisted Intervention (MICCAI), 14(2), 191-199 (2008); O'Donnell et al., AJNR. American journal of neuroradiology, 27(5), 1032-6 (2006); Tunç et al., 2013, cited above). As an alternative to fiber tractography based approaches, another set of supervised methods have been proposed for direct segmentation of WM tracts by classification using voxel-based features such as principal diffusion direction, spherical harmonics coefficients, fractional anisotropy (FA) values, and crossing angles [Bazin et al., NeuroImage, 58(2), 458-68 (2011); Ito et al., Magnetic resonance in medical sciences, 12(3), 201-13 (2013); Nazem-Zadeh et al., NeuroImage, 54, 146-164 (2011); W. Zhang et al., NeuroImage, 42(2), 771-7 (2008)].

The most common way of tract extraction is generating fiber pathways for the whole brain and then using multiple inclusion and exclusion ROIs, that could be chosen based on an anatomical atlas that is registered to the subject [Mori & van Zijl, Fiber tracking: principles and strategies—a technical review. NMR in biomedicine, 15(7-8), 468-80 (2002); Wakana et al., Fiber tracking: principles and strategies—a technical review. NMR in biomedicine, 15(7-8), 468-80 (2007)]. The main drawback with these multiple regions of interest (MROI) techniques is the fact that one needs to know which ROIs are to be used specifically for each TOI, which requires a detailed knowledge of the anatomy. Several authors have proposed improvements on automating selection of initial seed points and the ROIs, and on addressing registration issues for group studies [Li et al., NeuroImage, 49(2), 1249-58 (2010); Suarez et al., NeuroImage, 49(2), 1249-58 (2012); W. Zhang et al., NeuroImage, 42(2), 771-7 (2008); Y. Zhang et al., NeuroImage, 42(2), 771-7 (2010)]. However, these improvements cannot alleviate the need for knowing the anatomy of each TOI beforehand.

Once fibers have been generated for the full brain, instead of using the supervised MROI techniques, unsupervised clustering of fibers has emerged as a promising alternative to automate tract extraction by grouping the fiber pathways according to some predefined features such as geometrical or connectivity based measures [Brun et al., Medical Image Computing and Computer-Assisted Intervention (MICCAI), 3216/2004 (3216), 368-375 (2004); Liu et al., Unsupervised Automatic White Matter Fiber Clustering Using A Gaussian Mixture Model. Proceedings of IEEE International Symposium on Biomedical Imaging, 2012(9), 522-525 (2012); Maddah et al., Medical image analysis, 12(2), 191-202 (2008); O'Donnell et al., AJNR. American journal of neuroradiology, 27(5), 1032-6 (2006); Q. Wang et al., Hierarchical fiber clustering based on multi-scale neuroanatomical features. In Proceedings of the international conference on Medical imaging and augmented reality (pp. 448-456). Springer-Verlag (2010); Wassermann et al., NeuroImage, 51(1), 228-41 (2010)]. The resulting fiber bundles delineate different characteristics of white matter depending on which features are described by the underlying fiber representation. Fiber clustering and MROI approaches were compared in [Voineskos et al., NeuroImage, 45(2), 370-6 (2009)] to estimate the confidence bounds of fiber clustering with respect to the manual selection, concluding that fiber clustering can be used with a high confidence. Despite the ease of the unsupervised clustering, these methods mainly suffer from the difficulty in setting up the correspondence between subjects, or may use an incomplete representation of the underlying data, using just the shape information of fibers.

Early works on fiber clustering did not facilitate automated correspondence of TOIs across subjects. Some research has been done on establishing the correspondence across subjects after clustering each subject individually [Ge et al., Medical Image Computing and Computer-Assisted Intervention (MICCAI), 15(3), 485-92 (2012); Guevara et al., NeuroImage, 61(4), 1083-99 (2012)]. One drawback of these methods is that clustering of a subject is not guided in any way by the information from other subjects. Several recent works addressed the automated correspondence problem by combining fibers of different subjects and clustering them together. In Maddah et al. [Sheet-like white matter fiber tracts: representation, clustering, and quantitative analysis. Medical Image Computing and Computer-Assisted Intervention (MICCAI), 14(2), 191-199 (2011)], registration of fibers is handled together with clustering by using the expectation maximization (EM) algorithm [Dempster et al., Journal of the Royal Statistical Society B, 39(1), 1-38 (1977)], to generate a clustering atlas. Clustering of new subjects based on previously generated atlases is studied in [O'Donnell & Westin, IEEE transactions on medical imaging, 26(11), 1562-75 (2007); X. Wang et al., NeuroImage, 54(1), 290-302 (2011)]. These works introduced a new perspective of building clustering atlases to enable the WM tract analysis in large scale clinical studies [O'Donnell et al., NeuroImage, 80, 283-289 (2013)].

In real life clinical applications, one requires a group wise and longitudinally consistent TOI extraction method, so that statistical analyses can be performed subsequently. Moreover, the proposed method should be able to cluster the fibers of a new subject adaptively in a way that the correspondence with other subjects in the population is automatically established, without re-running clustering over the whole sample.

Surgical resection of gliomas continues to be a challenge due to their diffuse, infiltrative nature [Abdullah K G, et al, Neurosurg Focus. 2013; 34(4):E1]. Because of the survival benefits of maximal resection, [Brem S S, et al. J Natl Compr Canc Netw. 2011; 9(4):352-400; Sanai N, et al, Neurosurgery. 2008; 62(4):753-764; discussion 264-266; Eyüpoglu I Y, et al, Nat Rev Neurol. 2013; 9(3):141-151; Sanai N, et al., J Neurosurg. 2011; 115(1):3-82-5] an objective of neurosurgical oncology is to determine the optimal resection margin while preserving language, visual and motor function. Consequently, the localization of eloquent cortical regions as well as white matter pathways in the tumor margin is essential to decrease patient morbidity.

Current surgical planning relies heavily on MRI to visualize anatomic structures [Nimsky C, et al., Neurosurgery. 2005; 56(1):130-137; Golby A J, et al., Neurosurgery. 2011; 68(2):496-5056]. Diffusion tensor imaging (DTI) [Basser P J, et al., Biophys J. 1994; 66:259-267] and fiber tractography [Basser P J, et al, Magn Reson Med. 2000; 44(4):625-632; Mori S and van Zijl P, Fiber tracking: principles and strategies—a technical review. NMR Biomed. 2002; 15(7-8):468-480; Behrens T E J, et al., Neuroimage. 2007; 34(1):144-1559] are used to visualize the anatomic relationship between white matter fibers and the surgical target in order to guide the surgical approach and maximize the extent of resection while preserving function [Nisky et al, cited above; Lerner A, et al, Clinical Applications of Diffusion Tensor Imaging. World Neurosurg. 2013; Nimsky C, et al., Neurosurgery. 2007; 61 (Supplement):178-186]. In current clinical practice, pre-operative DTI-based tract identification is typically achieved by restricting the whole brain tractography with regions of interest (ROIs) selected by a surgeon or radiologist. However, the selection of these ROIs becomes problematic when the fibers in the white matter are altered by edema, infiltration, mass effect, or shift. These challenges render the manual placement of ROIs time-consuming and introduce significant inter- and intra-expert variability. Moreover, the variability is compounded when isolating a tract across multiple time points, e.g., pre- and post-operatively.

Automated tract identification methods, based on fiber clustering, groups individual fibers into bundles depending on their shape and characteristics of the white matter. Software-based automation has emerged as a promising alternative to the manual drawing of ROIs [Wassermann D, et al, Neuroimage. 2010; 51(1):228-241; Maddah M, et al., Med Image Anal. 2008; 12(2):191-202; O'Donnell L J, et al, AJNR Am J Neuroradiol. 2006; 27(5): 1032-1036; Wu G, et al., Hum Brain Mapp. 2012; 33(2):253-271; Tunç B, et al, Multinomial probabilistic fiber representation for connectivity driven clustering. In: Information Processing in Medical Imaging (IPMI). Lecture Notes in Computer Science; 2013:730-741] however, existing methods have been mostly applied to identifying healthy tracts, with a few studies including patients with brain tumors [Zhang W, et al, Neuroimage. 2008; 42(2):771-777; O'Donnell L J, et al, fMRI-DTI modeling via landmark distance atlases for prediction and detection of fiber tracts. Neuroimage. 2012; 60(1):456-47020, 21] since the methods utilize fiber shape and location and thus are inapplicable when the fibers are perturbed by mass effect or infiltration.

SUMMARY OF THE INVENTION

This specification provides an innovative connectivity-based clustering method for the automated identification of white matter tracts, including those that are disrupted and/or displaced in the presence of mass effect and/or edema. The method addresses the subjectivity and variability of manual region-of-interest (ROI) placement which is associated with currently used methods.

In one aspect, a method for processing diffusion data for identification of white matter tracts in the brain of a patient is provided. The method comprises, with a processor: (a) generating a connectivity based representation of white matter fibers for multiple different subjects from the connectivity signatures of the fibers from a diffusion magnetic resonance imaging (dMRI) without using the physical coordinates of the fibers; (b) generating a fiber bundle atlas from the connectivity based fiber representation of (a) which define a model of the human brain; (c) adaptively clustering fibers of a new patient utilizing the fiber bundle atlas of (b)

to extract white matter tracts; and (d) presenting the selected white matter tracts and diffusion data in a report or on a display device.

In another aspect, a non-transitory computer readable medium carrying software for controlling a processor is described herein. This medium and software carry out the method described herein for processing diffusion data for identification of white matter tracts in the brain of a patient.

In still another aspect, a diffusion data processing apparatus is described, which is useful for performing white matter tract-based analysis with large samples, said apparatus comprising: (a) a connectivity based fiber contents processor arranged to permit comparison or combination of fibers of multiple different subjects which utilizes the connectivity signatures of the fibers from a diffusion magnetic resonance imaging (dMRI) without using the physical coordinates of the fibers; (b) a fiber bundle apparatus processor which defines an atlas of the fiber bundles in the human brain; and (c) a clustering processor arranged to adaptively cluster fibers of a new patient utilizing the fiber bundle atlas of (b).

In another aspect, an imaging system is described which comprises a diffusion magnetic resonance imaging apparatus and the data processing apparatus described herein.

In still a further aspect, a diffusion magnetic resonance imaging apparatus is described which comprises: (a) a diffusion magnetic resonance imaging (dMRI) apparatus for obtaining diffusion data; (b) a connectivity based fiber contents processor arranged to permit comparison or combination of fibers of multiple different subjects which utilizes the connectivity signatures of the fibers from the dMRI without using the physical coordinates of the fibers; (c) a fiber bundle apparatus processor which defines a model of the fiber bundles in the human brain; and (d) a clustering processor arranged to adaptively cluster fibers of a new patient utilizing the fiber bundle atlas of (c); and (e) an output device which outputs or displays a report.

In yet another aspect, a method for designing a treatment plan for glioma patients in the optional presence of edema, mass effect and/or tract infiltration, using a processor, is described. The method comprises (a) generating a connectivity based representation of white matter fibers for multiple different subjects from the connectivity signatures of the fibers from a diffusion magnetic resonance imaging (dMRI) without using the physical coordinates of the fibers; (b) generating a fiber bundle atlas from the connectivity based fiber representation of (a) which define a model of the human brain; (c) adaptively clustering fibers of a glioma patient utilizing the fiber bundle atlas of (b); and (e) presenting the diffusion data in a report or on a display device.

Still other aspects and advantages of the invention will be apparent from the following detailed description of the invention.

BRIEF DESCRIPTION OF THE DRAWINGS

FIG. 1 provides an illustration of the process to generate the connectivity based fiber representation. (1) The multinomial representation for a single fiber. The matrix is prepared by stacking connectivity vectors, corresponding to each voxel, as its rows. (2) The compact representation of the fiber is generated by averaging over voxels. (3) The same procedure is repeated for each fiber, resulting in a matrix representation of the bundle.

FIGS. 2A-2D show clusters of the corpus callosum for four subjects when each subject is clustered individually. The difference in clustering hinders reliable correspondence and hence comparison across the bundles of the subjects. The colors do not represent correspondence among bundles.

FIGS. 7A-7F show clustering of the corpus callosum for two different subjects (top and bottom), each repeated three times by changing the atlas subjects. Each row shows the within subject variation of clustering results for a single subject while between subjects consistency is presented in the columns. The within subject variation is minimal for both subjects, showing promising robustness to changing the atlas subjects.

FIGS. 14A-14D is an illustration of the WM fibers in the internal capsule in the atlas (first, FIG. 14A), a healthy subject (second, FIG. 14B), and a patient with a brain tumor and a prior surgical site (third, FIG. 14C). Surrounding edema around the tumor and resection volume is also shown in FIG. 14D. The internal capsule was successfully identified by adaptive clustering in both healthy subject and the patient with the tumor despite the presence of large mass effect.

DETAILED DISCLOSURE OF THE INVENTION

Figure 3E:
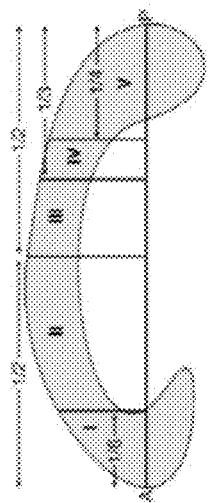
FIGS. 3A-3F shows the clusters of the corpus callosum for the same set of subjects that are displayed in FIGS. 2A-2D with clustering being run over the combined set of fibers collected from all subjects. The third column (FIGS. 3E-3F) shows the anatomical parcellation of the corpus callosum, as the proposed ground truth to be compared against. The colors are used to represent the correspondence across subjects that was achieved automatically.
Figure 3F:
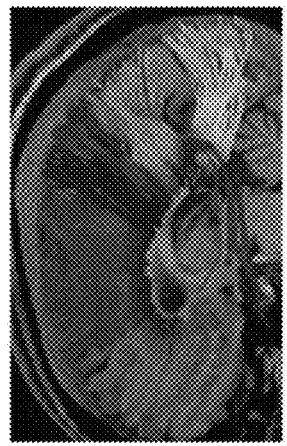
Figure 3B:
Figure 3D:
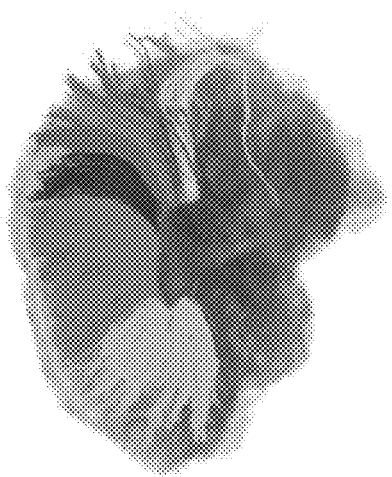
Figure 3A:
Figure 3C:

The present invention provides a method and apparatus for automated extraction of white matter tracts. The process and apparatus comprises three components, namely a connectivity based fiber representation, a fiber clustering atlas, and a clustering approach called Adaptive Clustering. In one embodiment, all three components are used in combination with each other. In another embodiment, one or two of these components may be used in combination with other components, e.g., the connectivity based fiber representation may be used for other applications, or a different representation can be used with an atlas and clustering approach. Still other alternative uses of these components will be clear from the following description.

In summary, the fiber representation described herein relies on the connectivity signatures of fibers to establish an easy correspondence between different subjects. A groupwise clustering of these fibers that are represented by the connectivity signatures is then used to generate a fiber bundle atlas as described herein. Finally, Adaptive Clustering as described herein incorporates the previously generated clustering atlas as a prior, to cluster the fibers of a new subject automatically. Experiments on the HARDI scans of healthy individuals acquired repeatedly, demonstrate the applicability, the reliability and the repeatability of our approach in extracting white matter tracts. By alleviating the seed region selection or the inclusion/exclusion ROI drawing requirements that are usually handled by trained radiologists, the proposed framework expands the range of possible clinical applications and establishes the ability to perform tract-based analyses with large samples.

The method and apparatus disclosed herein permit disease trajectory and response to therapy to be mapped in a variety of neurological diseases, including brain tumors.

In one aspect, the invention provides a method for automated identification of white matter tracts which facilitates longitudinal, quantitative characterization of white matter changes. Such sequential changes are difficult to assess using currently available methods, due to a lack of reproducibility when identifying white matter tracts.

As used herein, each single pathway of tractography is referred to as "fiber". Groups of fibers are called "fiber bundles". The term "tract" is used to refer to "a white matter (WM) structure of interest" such as the arcuate or the corpus callosum, which can consist of a single (the arcuate) or multiple (the corpus callosum) fiber bundles.

As used herein, the term "about" refers to a value+/−10% to the reference numerical value provided, unless otherwise specified.

The terms "comprising", "comprise", "contain", include, and their variants are open to other elements or components. In contrast, the terms "consisting", "consists", and its variants is closed to other elements or components.

In one aspect, the process described herein utilizes at least one processor, and optionally, at least one software program. Each at least one software program is independently, and optionally, provided in a non-transitory computer readable medium (e.g., a hard drive, CD, DVD, or the like) carrying the software.

As used herein, the term "processor" refers to a functional unit that interprets and executes instruction data. Such a functional unit may be, e.g., a computer, a diffusion data apparatus, a hand-held device or other apparatus or equipment.

As described herein, computer software may be operably linked to a processor or other apparatus.

The process described herein may start with the data provided by an imaging system, e.g., a diffusion magnetic resonance imaging (MRI) apparatus. Although the examples below refer to a Siemens 3T Vero™ scanner with a defined diffusion and MP-RAGE imaging sequence, it will be understood by one of skill in the art that the process and apparatus described herein are not limited to this equipment, settings, sequences, or imaging and tractography package. A variety of suitable imaging systems are commercially available, e.g., from Siemens, GE, Philips, Hitachi or Toshiba. The imaging system and dMRI are not a limitation on the present invention. The apparatus provided herein may be integrated with the imaging apparatus, or separate from, and operably linked so that the data from the dMRI is transmitted electronically to apparatus described herein. Alternatively, the processor(s) described herein are not directly operably linked to receive the data output of the imaging system, but is a stand-alone system to which the data are delivered by separate means. The manner in which the starting data are delivered to a processor as described herein, is not a limit on the present invention.

Connectivity Based Fiber Representation

Current (prior art) fiber representations primarily encode information on the geometric attributes of fibers by treating them as sampled 3D curves [Maddah et al., (2008) Med Image Anal, 12(2): 191-202; O'Donnell et al., (2006) AJNR Am J Neuroradiol 27(5): 1032-1036]. Abstraction of those geometric features into other mathematical objects such as Gaussian processes [Wassermann et al., (2010) NeuroImage, 51(1): 228-241] or Gaussian mixture models [Liu et al., (2012) Proceedings of IEEE International Symposium on Biomedical Imaging, 9: 522-525] has been practiced to extract more reliable shape information.

While using high level shape information such as length and curvature may alleviate the dependence on the physical coordinates, such representations can only provide geometric features without incorporating any information related to the diffusion data such as connectivity and integrity, limiting the interpretability of the selected representation.

Analyzing fiber bundles across individuals or groups to identify the personal characteristics or the group differences requires a reliable fiber correspondence among different subjects. This is a very challenging task since it is not possible to compare fibers having different coordinate systems without registering them. The method provided herein addresses this problem by using the connectivity signatures of fibers.

The multinomial connectivity signature of a fiber is a collection of voxels that it traverses and their corresponding probabilistic connectivity signatures. In one embodiment, the process provided herein defines a parcellation of the brain into regions (G_i), e.g. important cortical regions, by mapping an anatomical atlas including these regions to each subject. In the working examples below, FreeSurfer [http://surfer.nmr.mgh.harvard.edu/] was used to parcellate the brain of healthy subjects into 95 regions [Desikan et al., NeuroImage, 31(3):968-80 (Jul. 1, 2006) and DRAMMS [Y Ou, et al, Med Image Anal. 2011; 15(4): 622-639] was used for patients. However, one of skill in the art will readily understand that other number of regions may be used, e.g., from about 80 to about 5000, or values there between, or higher or lower. Further, other methods or algorithms may be selected by one skilled in the art. Examples of such other methods for brain parcellation are described, e.g., Klein and Tourville, 2012, 101 labeled brain images and a consistent human cortical labeling protocol. Front. Neurosci. 6:171; Roca, P., et al., (2010). Inter-subject connectivity-based parcellation of a patch of cerebral cortex. Med. Image. Comput. Comput. Assist. Interv. 13(Pt 2), 347-354; Mazziotta et al., (2001). A probabilistic atlas and reference system for the human brain: international consortium for brain mapping (icbm). Philos. Trans. R. Soc. Lond. B Biol. Sci. 356, 1293-1322; Tzourio-Mazoyer et al., (2002). Automated anatomical labeling of activations in spm using a macroscopic anatomical parcellation of the mni MRI single-subject brain. Neuroimage 15, 273-289; Shattuck et al., (2008). Construction of a 3d probabilistic atlas of human cortical structures. Neuroimage 39, 1064-1080 and those reviewed in E. Bujnoskova, et al, Clinical Neurophysiology, Vol. 125, Issue 5, pages 231-e32; R. C. Craddock, et al, Nature Methods, 10: 524-539 (2013). Alternatively, other methods of deformable registration may be used. Then, the connectivity signature u(x) of each voxel x is defined as the collection of the connection probabilities of the voxel to these regions $G_i$, resulting in an M dimensional multinomial vector, where M is the number of regions.

$$u(x)=[p(G_1|x),p(G_2|x),\ldots,p(G_M|x)]. \quad (1)$$

Each posterior probability $p(G_i|x)$ is first calculated by counting the number of fibers passing through the voxel x and finally connecting to the region $G_i$. Then, the values are normalized for each voxel so as to sum to 1.

Then, a fiber is naturally represented by a matrix having the connectivity vectors u(x) as its rows or columns. An illustrative example for a fiber selected from the corpus callosum is given in FIG. 1. The matrix clearly favors two regions, namely the ones at the ends of the fiber. The main intuition behind the probabilistic representation is the enhancement of the results of tractography with the notion of uncertainty. This enhancement is especially helpful in fiber clustering as it affords additional information for separating fibers with respect to using only the two regions marking the ends of the fiber.

The matrix representation of fibers may introduce complexities with fiber clustering since it is necessary either to define a proper metric for fibers of varying lengths or to introduce an extra fiber parameterization step to have equal lengths fibers. Hence, instead of working with the matrix representations, the weighted average over voxels to have a compact representation of a fiber. Different weights over voxels are used to emphasize the contributions of the specific voxels such as endpoints [Tunç et al., Information Processing in Medical Imaging (IPMI) (2013)]. A weight function that assigns higher weights to the endpoints and symmetrically decreases towards the center was used. Finally, each fiber f is represented by a single multinomial vector $$F=[p(G_1|f),p(G_2|f),\ldots,p(G_M|f)], \quad (2)$$

where the posterior probability $p(G_i|f)$ is calculated by averaging over voxels of the fiber f and then by normalizing so as to sum to 1.

Using the multinomial representation of fibers and the GMM or the MMN clustering algorithm, a clustering framework is defined that produces highly consistent fiber bundles for a large group of individuals. The clustering approach is described in detail in the next two sections. Optionally, the clustering approach described below may be used with a hierarchal multinomial representation of fibers that utilizes a differential approach at each level.

Fiber Bundle Atlas

While the fiber bundle atlas described in this section is desirably used with the connectivity based fiber representation described in this specification, it may alternatively be used with another representation such as the conventional geometric ones, as long as the fibers of all subjects are registered to a common template.

When clustered individually as is the case in prior art methods, fiber bundles of different subjects are mostly incompatible due to the subject specific characteristics of fibers. FIG. 2 illustrates this behavior for clustering of the corpus callosum of four subjects when the GMM is employed as the clustering algorithm.

A. Mixture of Gaussians Model (MGM)

To assure the correspondence among subjects, each subject is assumed to be an independent observation from the underlying common bundle model, i.e. an atlas of fiber bundles. The easiest way to define such a fiber bundle atlas is merging fibers of all subjects and clustering over the combined set. The resulting GMM is a parameterization of the atlas, with each Gaussian representing a common fiber bundle. This approach can be applied easily to the multinomial representation (see section Connectivity Based Fiber Representation) since it does not require registration of fibers. FIG. 3 shows the fiber bundles of the subjects that were used in FIG. 2, after combining fibers and clustering over the combined set. The anatomical parcellation of the corpus callosum as provided in [Hofer & Frahm, (2006) NeuroImage, 32(3): 989-994] is also illustrated in FIG. 3 for comparison purposes. In one illustrative study, the corpus callosum is clustered into twenty clusters, which clusters are subsequently labeled to get improved correspondence to the anatomical division.

When compared to FIG. 2, a substantial improvement in consistency is observed between fiber bundles of subjects in FIG. 3. However, combining fibers of all subjects poses some challenges. First of all, individual differences may be suppressed. This hinders capturing any important anomaly in the group. Second, this procedure is space intensive as thousands (even millions) of fibers will be combined. A prior art approach to get around this problem is using sampling or multi-scale approaches to decrease the amount of pairwise distance calculations between fibers [Guevara et al., (2011) "Segmentation of short association bundles in massive tractography datasets using a multi-subject bundle atlas. In: San Martin, C., et al, (eds) Progress in Pattern Recognition, Image Analysis, Computer Vision, and Applications, vol. 7042. Springer Berlin Heidelberg, Berlin, Heidelberg, pp. 701-708]; O'Donnell & Westin (2007), IEEE Trans Med Imaging, 26(11): 1562-1575; Visser et al., (2011) NeuroImage, 54(1): 303-312].

Here, a different approach to address these problems is described, after elaborating some notations that will be used throughout this specification. When using the GMM for clustering, it generates a set of Gaussian distributions parameterized by $(\mu_i, \Sigma_i, \pi_i)$, i=1 . . . C, where "C" is the number of clusters in the mixture. Here, $\mu_i$ is the mean vector (the mean connectivity signature of the fibers assigned to the i^th cluster), $\Sigma_i$ is the covariance matrix, and $\pi_i$ is the prior of this cluster (the ratio of the number of the fibers assigned to this cluster over the total number of fibers of the subject). Each distribution corresponds to a cluster and therefore a fiber bundle. Each fiber f that is represented by the multinomial vector F (equation 2) is assigned to the i^th bundle by the posterior probability $p(i|F, \mu_i, \Sigma_i, \pi_i)$.

$$p(i|F, \mu_i, \Sigma_i, \pi_i) = \frac{\pi_i p(F|\mu_i, \Sigma_i)}{\sum_j^C \pi_j p(F|\mu_j, \Sigma_j)} \quad (3)$$

where the probability, p $(F|\mu_i, \Sigma_i)$ is the likelihood of the multivariate normal distribution parameterized by $(\mu_i, \Sigma_i)$.

An online version (i.e. incremental training scheme) of the GMM as defined in (Song & Wang, (2005) Highly efficient incremental estimation of Gaussian mixture models for online data stream clustering. In: Priddy, K. L. (ed), Intelligent Computing: Theory and Applications III. Vol. 5803, pp. 174-183) to decrease the space complexity of the atlas generation, which allows building the atlas incrementally by merging fiber bundles of subjects. Two modifications in the original algorithm of (Song & Wang, 2005, cited above) are described herein. First, a new distance measure between fiber bundles is used and second, a new decision step for merging bundles is introduced. A novel online GMM algorithm is detailed in Table 1. As used herein, the term "online GMIM" indicates that the algorithm is updated iteratively as new data arrives.

TABLE 1

Algorithm of the modified GMM.

Given a set of subjects = $\{S_1, S_2, ... , S_L\}$ , the number of clusters C, and the distance threshold τ,
1. Cluster all subjects individually and parameterize results as ($\mu_{ij}, \Sigma_{ij}, \pi_{ij}$), i=1...L ; j=1...C
2. Define $S_1$ as the initial atlas, T = $S_1$ and $\hat{C}$ = C ; ($\mu_{Tj}, \Sigma_{Tj}, \pi_{Tj}$), j=1...C
3. For subjects i=2...L
   a. Calculate distances ($d_{jk}$) between all pairs of bundles ($\mu_{Tj}, \Sigma_{Tj}$) and ($\mu_{ik}, \Sigma_{ik}$) using the Fréchet distance (equation (4))
   b. Match the bundles of T and $S_i$ using the Hungarian algorithm [Kuhn, Nav Res. Logist. Q, 2 (1-2): 83-97 (1955)]
   c. If the distance $d_{jk}$ between the matched bundles j and k is lower than τ, merge them using equations (5); add the resulting bundle as the j^th bundle of the atlas
   d. Otherwise, add the bundle k directly to the atlas as a new bundle and update $\hat{C}$, ($\hat{C} = \hat{C} + 1$)
4. Apply steps 3[a-d] to the bundles of the final atlas to merge any similar bundles Each subject is clustered individually, then fiber bundles are merged to generate a joint GMM. Given any two subjects, their fiber bundles are merged when the Fréchet distance [Dowson & Landau, (1982), J. Multivar. Anal. 12(3): 450-455] between them is lower than a threshold; otherwise, both bundles are directly added to the combined model. The final joint GMM consists of the merged bundles and the remaining single bundles of both subjects. The Fréchet distance between two multivariate normal distributions $D_1$ and $D_2$ is defined as $$d^2(D_1,D_2)=|\mu_1-\mu_2|^2+tr(\Sigma_1+\Sigma_2-2(\Sigma_1\Sigma_2)^{1/2}). \quad (4)$$

The merger of the bundles is performed by calculating a new mean vector, a covariance matrix, and a prior probability using the following formulas.

$$\hat{\mu} = \frac{N_1\pi_{1j}\mu_{1j} + N_2\pi_{2k}\mu_{2k}}{N_1\pi_{1j} + N_2\pi_{2k}}, \quad (5)$$

$$\hat{\Sigma} = \frac{N_1\pi_{1j}(\Sigma_{1j} + \mu_{1j}\mu'_{1j}) + N_2\pi_{2k}(\Sigma_{2k} + \mu_{2k}\mu'_{2k})}{N_1\pi_{1j} + N_2\pi_{2k}} - \hat{\mu}\hat{\mu}',$$

$$\hat{\pi} = \frac{N_1\pi_{1j} + N_2\pi_{2k}}{N_1 + N_2}.$$

In the above equations, $N_1$ and $N_2$ are the total number of fibers in the datasets of the subjects. The j^th bundle of the first subject is merged with the k^th bundle of the second subject to generate a new bundle characterized by ($\hat{\mu}, \hat{\Sigma}, \hat{\pi}$). $\pi_{1j}$ and $\pi_{2k}$ are the prior probabilities of the bundles in their GMMs, hence the quantities $N_1 \pi_{1j}$ and $N_2 \pi_{2k}$ give the number of fibers in the bundles j and k, respectively. For each remaining bundle that is not merged, its new prior probability in the joint GMM is calculated as $\hat{\pi}=N_1 \pi_{1j}/(N_1+N_2)$ if it comes from the first subject and $\hat{\pi}=N_2 \pi_{2j}/(N_1+N_2)$ otherwise.

Optionally, although currently less preferred, different models of clustering can be used as an alternative to the online GMM described herein. For example, an atlas may be generated by the MROI techniques, even though such an approach is computationally intensive.

Once the atlas is generated by either combining fibers of all subjects or using the online GMM, the resulting fiber bundles (clusters) are visually inspected and assigned labels indicating the WM structures to which they belong. This assures the automatic labeling of the bundles of a new subject that is clustered using Adaptive Clustering (explained in section Adaptive Clustering). See, e.g, Atlas of Human Grain Connections, Marco Catani, Michel Thiebaut de Schotten, Oxford University Press (2012).

B. Mixture of Multinomial (MMN) Clustering Model

An alternative to the Mixture of Gaussians Model (MGM) described above may be utilized. The main technical difference between The MMN model described herein and the GMM model is the way fiber bundles are represented in the model. Previously, fiber bundles were represented by Gaussian distributions, each parameterized by a mean vector and covariance matrix. MGM model poses several difficulties when the variation of bundles increases due to the distortion of white matter fibers by edema and mass effect. Specifically, the possible singularity of the covariance matrix due to high dimensionality hinders a successful atlas generation, and thereby automated extraction of bundles in a test subject. Thus, here a more stable model based on MMN is implemented that is not affected by dimensionality. In MMN, each fiber bundle is represented by a multinomial distribution, encoding the probabilities that fibers tend to connect gray matter regions.

The connectivity signature of a fiber is defined as a collection of connectivity signatures of voxels along the fiber [Tunc, 2013, Information Processing in Medical Imaging, pp. 730-741]. Given a parcellation of the brain into $K$ cortical regions $\{G_k\}$, the M dimensional vector $u(x)$ for a voxel x consists of connection probabilities, $u(x)=[\text{freq}(G_1|x), \text{freq}(G_2|x), \ldots, \text{freq}(G_K|x)]$, each corresponding to a connection to a specific region $G_k$ i.e. the number of fibers passing through the voxel x and connecting to region $G_k$. Then, a fiber is represented by a matrix with the vectors $u(x)$ as its rows or columns. Instead of working directly with matrices, the voxels are averaged along a fiber to obtain a compact representation. Such an approach eliminates any need to define a metric for matrices of varying sizes due to different number of voxels of fibers. Finally, each fiber is represented by a single vector $f=[f_1, f_2, \ldots, f_K]$, where $f_k$ is calculated by averaging frequencies, $\text{freq}(G_k|x)$, over voxels along the fiber [Tunc, 2013, cited above].

One important issue with fiber clustering is the fact that correspondence might not be easy to establish between the resulting fiber bundles of different subjects when they are clustered individually. To assure the correspondence among subjects, it is assumed that each subject is an independent observation from an underlying common bundle model that is characterized by a fiber bundle atlas.

An MMN model is used for clustering, which has been used for document clustering in the past. Each fiber is assumed to be drawn from a multinomial distribution, $f \sim MN(\beta)$. The probability mass function of a multinomial distribution is $$p(f|\beta) = \frac{n!}{f_1! \ldots f_K!} \beta_1^{f_1} \ldots \beta_K^{f_K}$$

where $n=\Sigma_k^K f_k$. Each element $\beta_k \geq 0$ gives the probability of being connected to a region $G_k$, where $\Sigma_k^K \beta_k = 1$. Fibers of the whole brain are assumed to be drawn from a mixture of M multinomial distributions, with the final likelihood of N fibers is $p(F|\lambda, B) = \Pi_i^N \Sigma_j^M \lambda_j p(f_i|\beta_j)$, where $\lambda_j$ is the weight of $j^{th}$ multinomial distribution. Given a set of fibers, the parameters $\lambda$ and B can be inferred by using the Expectation Maximization method. In the expectation step, the membership possibility is estimated as: $\gamma_i^j$ of the fiber i to the $j^{th}$ cluster by $$\gamma_i^j = \frac{p(f_i|\beta_j)}{\sum_v^m \lambda_v p(f_i|\beta_v)}. \tag{1A}$$

Then in the maximization step, the unknown parameters are estimated as $$\beta_{jk} = \frac{\sum_i^N \gamma_i^j f_{ik}}{\sum_i^N \gamma_i^j z_i}; z_i = \sum_k^K f_{ik}, \tag{2A}$$

$$\lambda_j = \frac{\sum_i^N \gamma_i^j}{N}. \tag{3A}$$

With a random initial guess on parameters, these two steps are repeated until convergence. Finally, the atlas is characterized by the defined mixture model, with each multinomial distribution corresponding to a fiber bundle. The resulting clusters are visually inspected by an expert to label them with white matter (WM) structures that they belong to.

Once the atlas is generated, it is used as a prior model for clustering fibers of a new subject. The adaptive clustering incorporates the generated atlas as a set of Dirichlet priors for the parameter set of the new MMN that is run for a test subject. For each multinomial distribution in the new model, a Dirichlet prior is defined: $\text{Dir}(\alpha_j)$ over the parameter $\beta_j$, where $\alpha_j$ is calculated by scaling the corresponding parameter $\hat{\beta}_j$ of the atlas, $\alpha_j = c\hat{\beta}_j$. Under these settings, the Maximum a Posteriori (MAP) estimate of the parameter $\beta$, given an observation (fiber) f is $$\beta_k = \frac{f_k + \alpha_k - 1}{z + \sum_v^K (\alpha_k - 1)}. \tag{4A}$$

Then, for clustering new subjects using the adaptive clustering scheme, the maximization step (2A) is modified as $$\beta_{jk} = \frac{\sum_i^N \gamma_i^j f_{ik} + \alpha_{jk} - 1}{\sum_i^N \gamma_i^j z_i + \alpha_j}; z_i = \sum_k^K f_{ik}; \alpha_j = \sum_k^K \alpha_{jk} - 1. \tag{5A}$$

In above formulation, the atlas introduces some pseudo counts for each cortical region. This means that one can adjust the compliance of a new subject with the atlas by changing the magnitudes of elements of $\alpha_j$ while keeping their proportions fixed.

Adaptive Clustering

The clustering atlas defines a common model for the fiber bundles of the human brain. Once the fiber bundles in the atlas are annotated, any TOI can be extracted simultaneously for all subjects since the TOI will be represented by the same Gaussian distribution(s) both in the atlas and in the fiber bundles set of any subject that is clustered adaptively using the atlas as a prior model.

The adaptive GMM [Reynolds et al., (2000) Digit. Signal Process, 10(1): 19-41] method is used in the examples herein; this technique is well known and commonly employed in the speech recognition literature. The usual way to estimate the parameters of a GMM is using the EM algorithm to maximize the data likelihood [Bishop, (2006) Pattern Recognition and Machine earning (Information Science and Statistics). Springer-Verlag New York, Inc., Secaucus, N.J.]. When a prior model (e.g., a bundle atlas) is to be introduced into clustering, the maximum a posteriori (MAP) parameter estimation (Reynolds et al., 2000, cited above) is used instead of EM. Given a new subject with a set of fibers new subject with a set of fibers $\{F_1, F_2, \ldots, F_N\}$, after clusters are initiated by the parameterization of the atlas, the following quantities are estimated in the expectation step.

$$n_i = \sum_{n=1}^{N} p(i \mid F_n, \mu_i, \Sigma_i, \pi_i), \qquad (6)$$

$$E_i[F] = \frac{1}{n_i} \sum_{n}^{N} p(i \mid F_n, \mu_i, \Sigma_i, \pi_i) F_n,$$

$$E_i[FF'] = \frac{1}{n_i} \sum_{n}^{N} p(i \mid F_n, \mu_i, \Sigma_i, \pi_i) F_n F_n',$$

Figure 4A:
FIGS. 4A-4B shows the clusters of the corpus callosum for two test subjects. Subjects are clustered adaptively, using the atlas displayed in FIGS. 3A-F as a prior model. The correspondence between the test and atlas subjects is noticeable (compare to FIGS. 3A-3F).
Figure 4B:
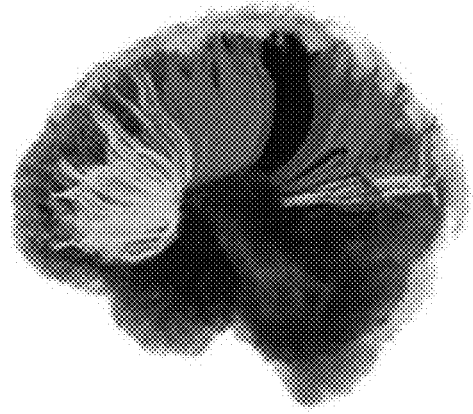

The posterior probability $p(i|F_n, \mu_i, \Sigma_i, \pi_i)$ is calculated by equation (3). Then, in the maximization step, the estimates for the parameters are adapted to the atlas as follows.

$$\pi_i = \lambda^\pi \frac{n_i}{N} + (1 - \lambda^\pi) \pi_{Ti}, \qquad (7)$$

$$\mu_i = \lambda^\mu E_i[F] + (1 - \lambda^\mu) \mu_{Ti},$$

$$\Sigma_i = \lambda^\Sigma E_i[FF'] + (1 - \lambda^\Sigma)(\Sigma_{Ti} + \mu_{Ti}\mu_{Ti}') - \mu_i\mu_i',$$

where the parameters $(\mu_{Ti}, \Sigma_{Ti}, \pi_{Ti})$ characterize the $i^{th}$ cluster of the atlas. The parameters $\lambda^\pi$, $\lambda^\mu$, and $\lambda^\Sigma$, with values between 0 and 1, control the tradeoff between the individual specifications of the subject and the compatibility to the atlas. Note that, $\pi_i$ must be normalized so as to sum to 1, after being calculated for all clusters. FIG. 4 shows illustrative fiber bundles of two test subjects when using Adaptive Clustering. In that example, the atlas was generated by merging four scans (see FIG. 3). This study illustrates that Adaptive Clustering provides high consistency across fiber bundles of subjects.

To summarize, the process described herein provides for the group-wise consistent clustering of fibers starting with the output of a diffusion imaging apparatus. A fiber clustering atlas is generated by clustering over the combined fibers of all subjects from a healthy sample. The combination of fibers of different subjects is achieved by defining a multinomial representation for the WM fibers that uses the underlying connectivity information. Then, a new subject is clustered adaptively by taking the atlas as a prior model. Adaptive Clustering grants an automated correspondence among fiber bundles of different subjects, each "adapted" from the same atlas.

The process addresses several problems with prior art techniques, by providing new fiber representation and clustering approach to automate TOI extraction for large groups of subjects, such that the extracted tracts have a correspondence established automatically. For any study dealing with group differences or longitudinal analyses over WM tracts, this is critical such that a joint comparative analysis can be performed. The unsupervised nature of fiber clustering eliminates the need for manually drawing any inclusion or exclusion ROI to define the TOI after tractography. Similarly, the determination of proper seed points to establish a clean and complete reconstruction of the TOI is not required. Human intervention may be needed labeling the bundles in the atlas; however, this is not a limiting feature since it enables us to define the TOIs with any desired precision.

Another important advantage of a clustering based approach over the MROI-based techniques is the ability to select the sub-bundles of large WM tracts in a very precise manner by controlling the number of clusters. For instance, when working with superior longitudinal fasciculus (SLF), a well formulated clustering scheme can extract SLF-I, SLF-II and SLF-III separately due to their different connectivity signatures. This improvement is essential for very large WM tracts such as the corpus callosum due to the effective heterogeneity in their neuroanatomical functioning. The usual way to study the corpus callosum is to segment it using an anatomical, geometrical, or histological parcellation. The ability to pinpoint the sub-bundles helps facilitate a detailed analysis of these tracts, as the sub-bundles are also in correspondence between subjects. Measures computed over these sub-bundles have greater specificity in identifying differences between subjects, than when the measures are computed over larger, more heterogeneous WM tracts. The number of clusters, in the current process, is determined in a semi-automated way. When using the online GMM provided in Table 1 above, the number of clusters for each subject is fixed manually. For example, the number of clusters may be in a range of about 100 to about 500, or higher or lower, depending upon the selected application. In one example, the number of clusters is about 200.

Then, depending on the merger/distance threshold (see Table 1), the final number of clusters in the atlas, and consequently for test subjects, is determined automatically. (The number of clusters in the atlas and in new subjects are the same.) The initial number of clusters as well as the threshold may change the resolution of the final result. One useful heuristic is to keep the initial number of clusters large enough to catch every meaningful sub-bundle of the important WM tracts. A large number of clusters does not increase the effort as labeling of the clusters is done only once for the atlas. Nevertheless, using a Bayesian approach may contribute with fully automating the task [X. Wang et al., (2011) Neuroimage, 54(1): 290-302].

The reproducibility of clustering results is critical for the most group and longitudinal studies. Considering the fact that the bundle atlas is prepared using the selected subjects, we expect that the results of Adaptive Clustering should not change substantially when the subjects are changed. This expected repeatability is validated both quantitatively and qualitatively in FIG. 6 and FIG. 7, respectively. On comparing the Fréchet distances in FIG. 6 with those of FIG. 5, changing the atlas subjects is observed to cause a difference in clustering results, that is as low as the difference between the fiber bundles of different time points of a single subject. As the number of subjects used in atlas building is increased, the robustness of the atlas improves while the total inter-subject variability increases due to broader anatomical variation.

Figure 6:
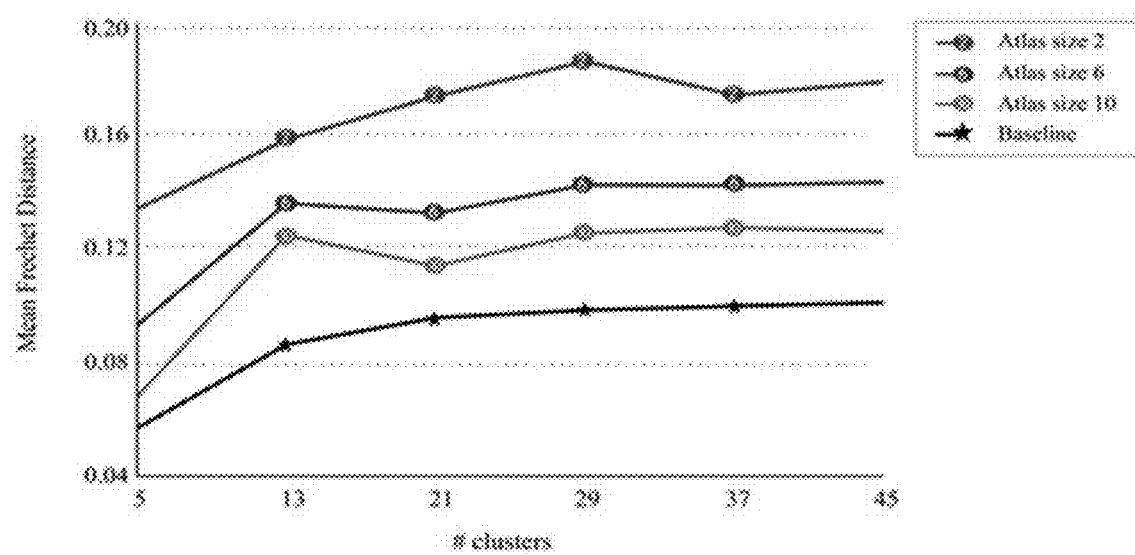
FIG. 6 provides the effect of changing the atlas subjects for Adaptive Clustering. A fixed test subject was clustered using several atlases, each built with different subjects, and the average Fréchet distances were computed between the matched bundles. The baseline distance is calculated by running a single GMM with different random initializations to illustrate an approximate lower bound for the Fréchet distance.
Figure 8:
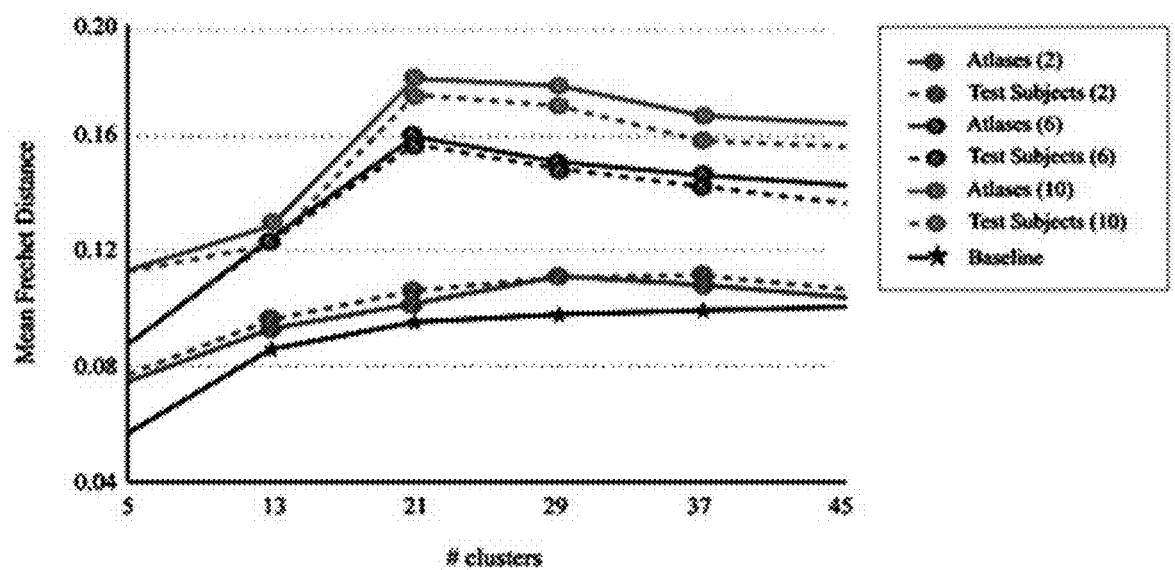
FIG. 8 shows the difference between using the traditional GMM and the online GMM to build an atlas. A test subject is clustered adaptively using two atlases generated by these two approaches. The average Fréchet distances both between the generated atlases and between the fiber bundles of the test subject are given. The size of the atlas is given in parenthesis. The baseline distance is calculated by running a single GMM with different random initializations to illustrate an approximate lower bound for the Fréchet distance. The difference between the results of traditional and online GMMs increases as the atlas size increases. This introduces a tradeoff between the reliability of the online GMM and the generalizability of the resulting atlas.
Figure 9A:
FIGS. 9A-9D show the application of Adaptive Clustering for group-wise consistent TOI extraction. The first row shows an atlas subject with all 327 clusters and selected WM tracts. Results for two test subjects are shown in the second and the third rows. The bundles (all from left hemisphere) corresponding to the internal capsule, the inferior fronto occipital fasciculus, the inferior longitudinal fasciculus, the arcuate fasciculus, and the uncinate are shown. It can be seen that while the fiber bundles are comparable, the individual variability is maintained.
Figure 9B:
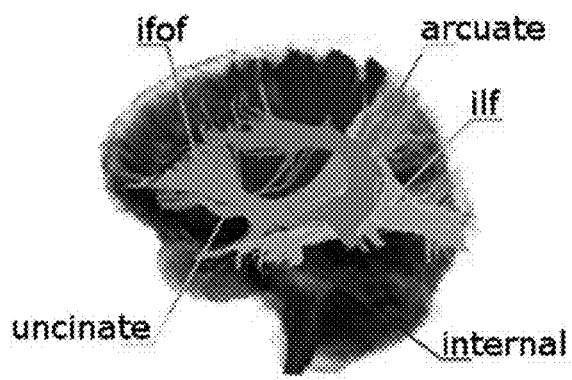
Figure 9C:
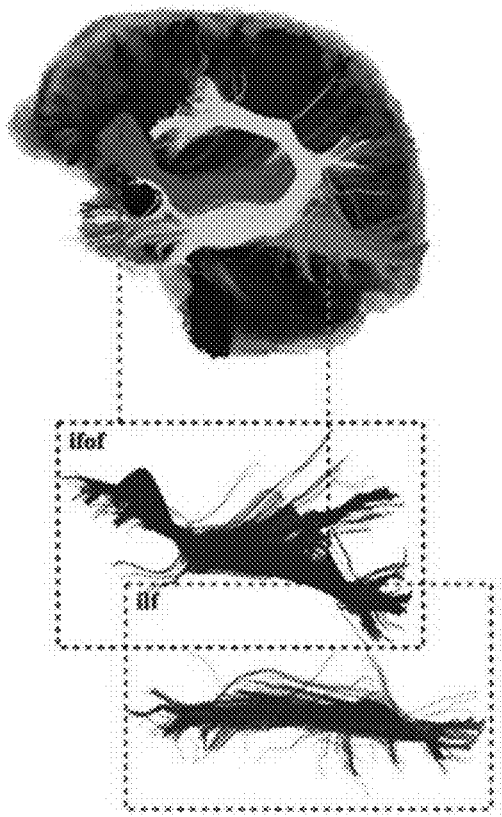
Figure 9D:
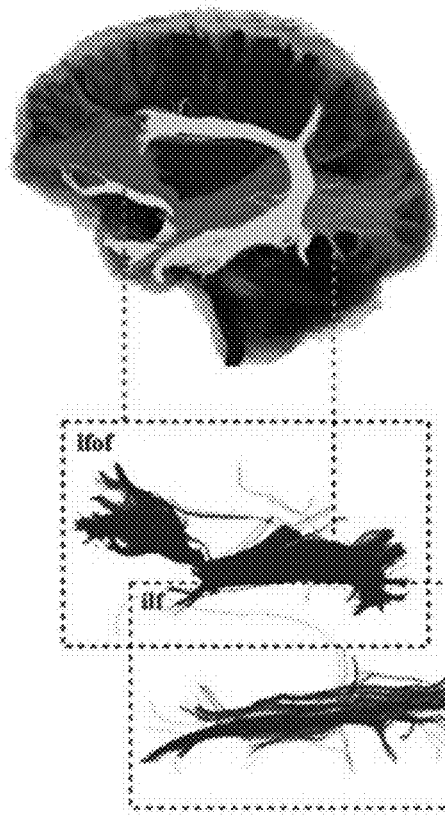
Figure 10A:
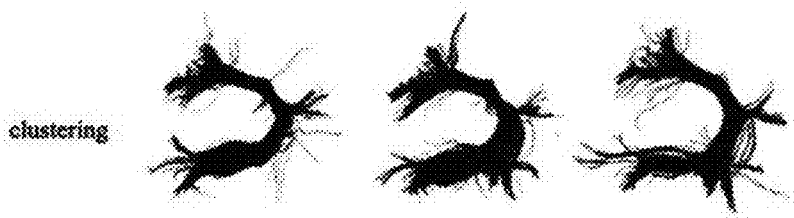
FIGS. 10A-10F show a comparison of the results of clustering with the manual reconstructions by experts. Results for the arcuate and the cingulum bundles of a single subject and three time points (columns) are given. For each bundle, the first row shows the results with clustering (FIGS. 10A and 10D) and other two with the expert drawings (FIGS. 10B and 10C, 10E and 10F, respectively). Visual evaluation shows a big overlap between results.
Figure 10B:
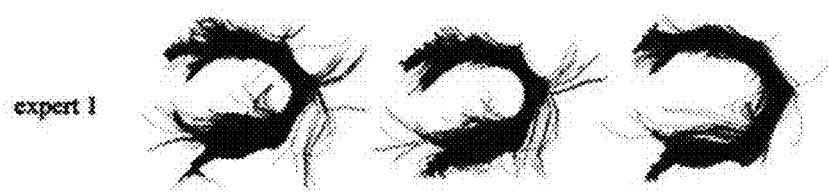
Figure 10C:
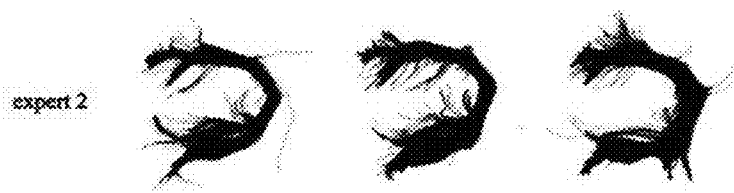
Figure 10D:
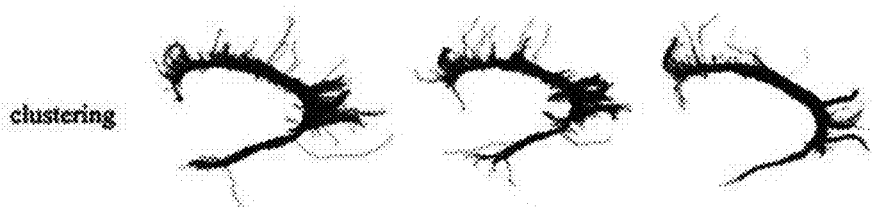
Figure 10E:
Figure 10F:

The challenge of space complexity in generating the atlas is resolved by use of the online GMM, that provides an efficient clustering strategy. Experiments using the online GMM for the atlas generation showed (FIG. 8) that incremental training approaches can be used instead of simply combining fibers of all subjects to generate an atlas, without causing a critical difference in the generated atlas or in clustering of a test subject. However, the difference between the atlases that are generated by the traditional GMM and the online GMM (as defined herein) tends to increase as the number of subjects used in the atlas generation is increased. This fact defines an important tradeoff. The number of subjects used in the atlas needs to be increased to make the resulting atlas a good representative of the sample (FIG. 6). On the other hand, the increase in the number of subjects reduces the reliability of the incremental approach (FIG. 8).

Figure 5:
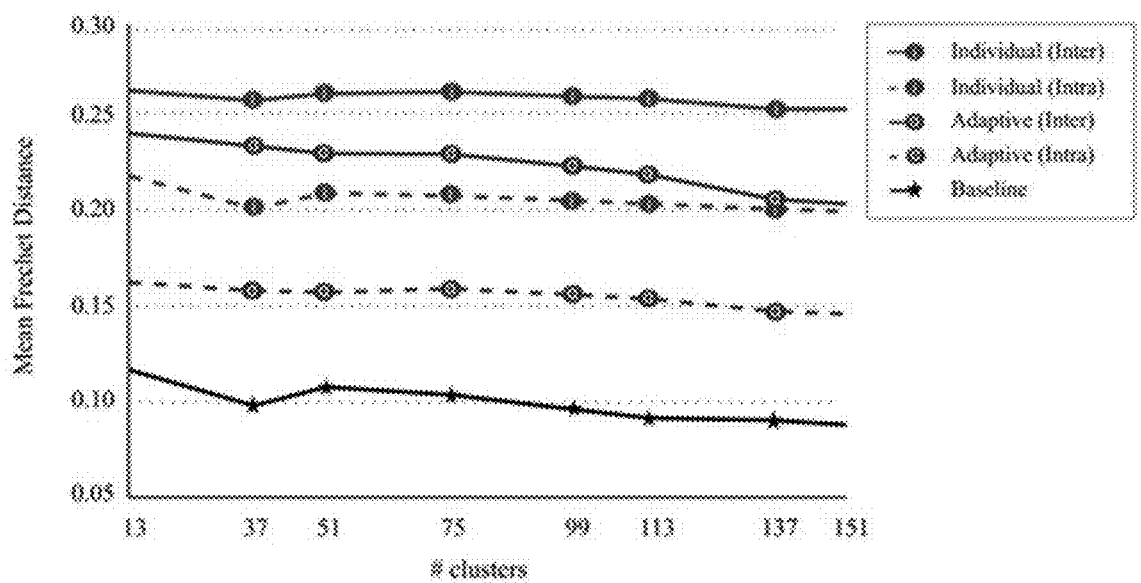
FIG. 5 shows the effect of Adaptive Clustering on the correspondence across fiber bundles. The average Fréchet distances were computed between the matched bundles of different subjects (inter) and different time points of a single subject (intra). The baseline distance is calculated by running a single GMM with different random initializations to illustrate an approximate lower bound for the Fréchet distance. Adaptive Clustering clearly decreases the average Fréchet distance, in both cases with the inter- and intra-subject comparisons.

The inter- and the intra-subject differences in FIG. 5 illustrate a promising aspect of the framework. Adaptive Clustering noticeably decreases both type of differences. Such a decrease in the difference of clustering results is the key element of the framework that affords group-wise consistent TOI extraction. Additionally, the fact that the intra-person differences are lower than the inter-person differences after Adaptive Clustering, illustrates the applicability of this method to personalized applications. For instance, person specific WM integrity measures along a TOI can be calculated and compared to the distribution of the whole sample since the distinction between the typical (i.e. specific to the group) and the individual (i.e. specific to the person) attributes is preserved.

Two successful applications of the framework were demonstrated with the whole brain tractography. For both experiments, four subjects were used for the atlas generation. The fiber bundles of the generated atlas were annotated once. Then by using the atlas as a prior model, the data corresponding to two remaining test subjects were clustered adaptively. Owing to the automated nature of the bundle correspondence between the novel subjects and the atlas, the TOIs of the test subjects were extracted automatically, without any manual intervention. Several WM tracts of the test subjects are illustrated in FIG. 9 and FIG. 10, demonstrating the notable success of the framework in automated TOI extraction. In the absence of histology, tracts drawn by experts were considered as "groundtruth". The comparison of the results of Adaptive Clustering with groundtruth was provided in FIG. 10. The visual comparisons suggest a promising overall agreement between experts drawings and the results of the clustering approach, which was also quantified by Sørensen-Dice (SD) index [Dice, Ecology, 26(3), 297-302 (1945); Sørensen, Kongelige Danske Videnskabemes Selskab, 5(4), 1-34 (1948)]. Two cases were investigated, one with a low agreement (the arcuate) and one with relatively higher agreement (the cingulum bundle). The main body of the TOI was extracted successfully in both cases while several fiber pathways were mistakenly excluded or included by the proposed framework that is mainly due to the unsupervised nature of clustering, or by experts due to slight differences in the ROI placement (see FIG. 9).

As described herein, a method for processing diffusion data for identification of white matter tracts in the brain of a patient is provided. Advantageously, the method may be used to identify white matter tracts in patients in the presence of edema, mass effect and/or tract infiltration. Such patients may include those with a variety of condition, including brain tumors.

The method comprises, with a processor: (a) generating a connectivity based representation of white matter fibers for multiple different subjects from the connectivity signatures of the fibers from a diffusion magnetic resonance imaging (dMRI) without using the physical coordinates of the fibers; (b) generating a fiber bundle atlas from the connectivity based fiber representation of (a) which define a model of the human brain; (c) adaptively clustering fibers of a new patient utilizing the fiber bundle atlas of (b) to extract white matter tracts; and (d) presenting the selected white matter tracts and diffusion data in a report or on a display device.

The connectivity based fiber representation may be constructed by (i) defining a parcellation of the brain of each of the multiple different subjects into regions by mapping an anatomic atlas including these regions to each of the subjects and (ii) determining the weighted average connectivity signatures over voxels of fibers to define a compact representation of each of the fibers from the multiple different subjects. Typically, in order to generate the atlas, the connectivity signature of the fibers of the multiple different subjects are incrementally merged from the connectivity representation and clusters over the combined set. The fiber bundles in the atlas are labelled to indicate the anatomic white matter structures to which the bundles correspond. Labelling may be performed using methods known to those of skill in the art. For example, the regions may be the cortical regions, e.g., selected from one or more of the primary motor cortex, Broca's area, orbitofrontal cortex, primary olfactory cortex, primary auditory cortex, Wernike's area, primary visual cortex, visual association area, primary gustatory cortex, somatosensory association cortex, primary somatosensory cortex/postcentral gyrus.

Subsequently, the scan results of a patient are assessed using the labelled atlas. In this manner, a track of interest (TOI) for a new patient is extracted from whole brain tractography results using the labelled atlas.

In an further aspect, a non-transitory computer readable medium is provided which carries software for controlling a processor to carry out the method described herein.

In still a further aspect, a diffusion data processing apparatus is provided which performs white matter tract-based analysis with large samples. Such an apparatus may comprise: a connectivity based fiber contents processor arranged to permit comparison or combination of fibers of multiple different subjects which utilizes the connectivity signatures of the fibers from a diffusion magnetic resonance imaging (dMRI) without using the physical coordinates of the fibers; a fiber bundle apparatus processor which defines an atlas of the fiber bundles in the human brain; and/or a clustering processor arranged to adaptively cluster fibers of a new patient utilizing the fiber bundle atlas. Optionally, the apparatus may contain a report generator and/or display device.

In yet another aspect, an imaging system is provided which comprises a diffusion magnetic resonance imaging apparatus and the data processing apparatus described herein.

A diffusion magnetic resonance imaging apparatus is described. This apparatus includes a diffusion magnetic resonance imaging (dMRI) apparatus for obtaining diffusion data; (b) a connectivity based fiber contents processor arranged to permit comparison or combination of fibers of multiple different subjects which utilizes the connectivity signatures of the fibers from the dMRI without using the physical coordinates of the fibers; (c) a fiber bundle apparatus processor which defines a model of the fiber bundles in the human brain; a clustering processor arranged to adaptively cluster fibers of a new patient utilizing the fiber bundle atlas; and an output device which outputs or displays a report.

The method and apparatus disclosed herein permit disease trajectory and response to therapy to be mapped in a variety of neurological diseases, including primary and metastatic brain tumors. These methods may be used as a sole diagnostic tool, or in conjunction with other assessments, including, e.g., CT scans. Examples of such neurological diseases, include, e.g., seizures; traumatic brain injury; nervous system disorders (such as, e.g., multiple sclerosis, Alzheimer's disease, Parkinson's disease, epilepsy, amyotrophic lateral sclerosis (ALS), and stroke); hydrocephalus; benign intracranial hypertension; cerebral atrophies; diseases of the blood vessels in the brain (including, e.g., stroke, transient ischemic attack (TIA), subarachnoid hemorrhage, subdural hemorrhage and hematoma, extradural hemorrhage, diabetic retinopathy; subarachnoid or intracranial hemorrhage); infections (such as meningitis, encephalitis, polio, and epidural abscess); depression; schizophrenia; hormonal disorders (e.g., acromegaly, galactorrhea, and Cushing syndrome); pituitary diseases; and cysts. Such brain tumors may be benign or cancerous tumors, and may located in different parts of the brain, e.g., supratentorial tumors, posterior fossa tumors. Examples of such brain tumors include, e.g., astrocytoma; atypical teratoid rhabioid tumor (ATRT); chondrosarcoma; choroid plexus; craniopharyngioma; cysts; ependymoma; germ cell tumor; glioblastoma; glioma; hemangioma; juvenile polocytic astrocytoma; lipoma; lymphoma; medulloblastoma; meningioma; neurofibroma, neuronal & mixed neuronal glial tumors; oligoastrocytoma; oligodendroglioma; pineal tumor; pituitary tumor; PNET; and schwannoma.

The methods and apparatus provided herein may be used for a patient presenting with such symptom as head trauma; concussion; muscle weakness, numbness or tingling; changes in thinking or behavior; hearing loss; headaches (when other symptoms are present); vision problems; speaking difficulties, among other symptoms.

The methods and apparatus provided herein provide valuable information for use by a diagnostician and clinician for designing treatment. Further, the effect of treatment and course of disease may be monitored using the methods and apparatus described herein.

In still another aspect, a method is provided which is useful in designing a treatment plan for glioma patients in the optional presence of edema, mass effect and/or tract infiltration, using a processor. The method involves generating a connectivity based representation of white matter fibers for multiple different subjects from the connectivity signatures of the fibers from a diffusion magnetic resonance imaging (dMRI) without using the physical coordinates of the fibers; generating a fiber bundle atlas from the connectivity based fiber representation of (a) which define a model of the human brain; adaptively clustering fibers of a glioma patient utilizing the fiber bundle atlas; and (e) presenting the diffusion data in a report or on a display device.

The following examples are illustrative of the invention, demonstrating generating an atlas using imaging data from healthy patients with two different embodiments and using the process on an illustrative test patient. Variations on the apparatus, settings, algorithms, and other aspects of the invention will be apparent to one of skill in the art.

EXAMPLES

Provided herein are a method and apparatus for automated extraction of the TOIs by introducing a group-wise consistent fiber clustering approach. This consists of firstly defining a connectivity based fiber representation, then using this representation to build a fiber bundle atlas, and finally an adaptive clustering of a new subject based on this atlas.

The following studies illustrate the applicability of this process in a pre-operative and treatment planning and compare the reliability of this technique with the current manual methodology. The process provided herein is able to identify eloquent tracts essential for surgical planning, as well as smaller tracts, that can be evaluated longitudinally to study treatment effects or to perform customized surgery that protects nuanced function.

In the following examples, the following abbreviations are utilized: TOI: Tract of interest; ROI: Region of interest; WM: White matter; AF: Arcuate fasciculus; CB: Cingulum bundle; DTI: Diffusion tensor imaging; FA: Fractional anisotropy; FR: Fornix; IFOF: Inferior fronto-occipital fasciculus; ILF: Inferior longitudinal fasciculus; UF: Uncinate fasciculus

Example 1

The following experiments were performed to demonstrate the applicability, the reliability and the repeatability of our approach using the high angular resolution diffusion-weighted imaging (HARDI) scans of six healthy individuals each having three scans acquired at different time points. With investigations provided below, the ability of the process described herein to group and longitudinal studies to extract TOIs were validated consistently across subjects.

Dataset

Imaging was performed on six healthy male subjects (Age 31.25±4.2 years) at three time points separated by two weeks. All participants were carefully screened to ensure that they did not have a history of current or prior neuropsychiatric symptomatology. For each subject at each time point, a whole brain HARDI dataset was acquired using a Siemens 3T Verio™ scanner using a monopolar Stejskal-Tanner diffusion weighted spin-echo, echo-planar imaging sequence (TR/TE=14.8s/111 ms, 2 mm isotropic voxels, b=3000 s/mm$^2$, number of diffusion directions=64, 2 b0 images, scan time 18 minutes). A structural image was acquired, using an MP-RAGE imaging sequence (TR/TE/TI=19s/2.54 ms/0.9s, 0.8 mm in plane resolution, 0.9 mm slice thickness) to facilitate the tissue segmentation. A gray matter (GM) parcellation was prepared for each HARDI scan including 95 GM regions, by applying FreeSurfer to the corresponding T1 image [Desikan et al., NeuroImage, 31(2); 968-980 (2006)], which is used for the connectivity measurements. Camino package [Cook et al., Camino: Open-Source Diffusion-MRI Reconstruction and Processing. In Scientific Meeting of the International Society for Magnetic Resonance in Medicine (p. 2759) (2006)] was used both for tractography and connectivity analysis.

A. Validation of Adaptive Clustering

The adaptive GMM model provided in this specification was assessed (Table 1) and shown to provide an increased correspondence among fiber bundles of different subjects or time points. Two subjects were selected as the test data and the remaining data corresponding to four subjects were used for the atlas generation. A single time point of each of the four atlas subjects was selected randomly. The data acquired at all three time points of the two test subjects were clustered adaptively using the generated atlas. Fibers from the whole brain tractography were used for this experiment. The intra-person distances (the distance between the fiber bundles of different time points of the same subject) and the inter-person distances (the distance between the fiber bundles of different subjects) were calculated. When calculating the average distance between two clustering results, the fiber bundles of the subjects/time points were first matched using a linear assignment algorithm [Kuhn, Naval Research Logistics Quarterly, 2(1-2), 83-97 (1955)], then the average of the Fréchet distances between the matched bundles was computed. [Other linear optimization methods may be substituted]. This experiment was repeated 100 times with the test and the atlas subjects/time points being selected randomly. The average intra- and inter-person distances were compared to those that are calculated when Adaptive Clustering is not used. FIG. 5 illustrates the effect of Adaptive Clustering. When Adaptive Clustering is used, both the intra- and the inter-person distances decrease to a great degree, as expected. To provide a better interpretation of the Fréchet distances a baseline distance (the black line in FIG. 5) was provided, by running a single GMM repeatedly with random initializations and calculating the distances between different runs. The baseline distance therefore defines an approximate lower limit that can be achieved, since we used random initializations in all experiments.

B. Invariance to Changing the Atlas Subjects

The repeatability of the framework was tested by fixing a randomly selected test subject and changing the atlas subjects repeatedly. None of the data acquired at any time point of the test subject were used in the atlas generation. The test subject was adaptively clustered, each time by a different atlas and the distances between clustering results were calculated by the Fréchet distance. The experiment was repeated with different number of clusters and atlas sizes (i.e. the number of subjects/time points used during the atlas generation). Only fibers seeded from the selected white matter regions, namely the corpus callosum, the corticospinal tract, the cingulum bundle, and the superior longitudinal fasciculus were used for this experiment. FIG. 6 shows results of the repeatability experiments. As we increase the atlas size, the effect of changing the atlas subjects decreases.

The repeatability of the framework is illustrated, this time qualitatively, in FIG. 7. For two test subjects, atlases were built three times by randomly changing the atlas subjects. Each time, four subjects out of the possible five subjects (excluding the subject that is used for testing) were selected with one dataset acquired at a single time point. The corpus callosum is clustered into twenty clusters, same as FIG. 3 and FIG. 4. The visual presentation in FIG. 7 together with the quantitative analysis in FIG. 6 demonstrates the high tolerance of Adaptive Clustering to changing the atlas subjects.

C. Reliability of the Online GMM

The online version of the GMM is proposed to decrease the high space complexity caused by combining fibers of all subjects during the atlas generation. It was hypothesized that clustering results of an incremental training approach will be very similar to those that are generated by simply combining fibers. This assumption was validated by comparing the results of the traditional GMM and the online GMM. For this experiment, a test subject was adaptively clustered, first using the atlas that is generated by combining fibers of all atlas subjects, and then using the atlas provided by the incremental approach. None of the data acquired at any time point of the test subject was used in the atlas generation. The distances between the generated atlases and the fiber bundles of the test subject were calculated. The experiment was repeated 100 times with the test and the atlas subjects/time points being selected randomly. FIG. 8 shows the calculated distances. In general, the difference in clustering results that are caused by using the incremental approach instead of combining fibers of all subjects, is as low as the difference that is caused by changing the atlas subjects (compare to FIG. 6). Thus, the incremental training can be used to decrease the space complexity of the atlas generation without introducing critical differences in clustering results.

D. Application for TOI Extraction

FIG. 9 and FIG. 10 show two successful applications of the proposed framework in group-wise consistent TOI extraction. Both experiments were performed using the whole brain tractography. An atlas was generated using four subjects and their data acquired at a single time point. Then, the data corresponding to all three time points of two test subjects were clustered adaptively. FIG. 9 shows the association tracts (the inferior fronto occipital fasciculus, the inferior longitudinal fasciculus, the arcuate fasciculus, and the uncinate fasciculus) and the internal capsule for the two test subjects, selected automatically after being annotated in the atlas once. The atlas was generated by using the online GMM. For each atlas subject the number of clusters was fixed as 200. This number was determined empirically, which is large enough to catch important sub-bundles of the WM tracts. The threshold for merging the clusters was determined as 0.23 (Fréchet distance). The final number of clusters as determined automatically (see Table 1) was 327. FIG. 9 shows all 327 clusters of an atlas subject together with the selected TOIs. The consistency between the fiber bundles of the test subjects and the atlas shows the effectiveness of the process of the invention.

In FIG. 10, two automatically extracted TOIs, namely the cingulum bundle and the arcuate of one of the test subjects are compared with those that are extracted manually with the inclusion and exclusion ROIs drawn by experts. Two experts extracted TOIs for the three time points of the test subject. FIG. 10 provides a visual insight into the agreement between experts and the clustering approach. As visual inspection shows, the proposed framework is successful in extracting WM tracts that are very similar to those drawn by experts with placement of the inclusion and exclusion ROIs that vary between experts. To provide a quantification of the agreement, the Sørensen-Dice (SD) index [Dice, Ecology, 26(3), 297-302 (1945); Sørensen, Kongelige Danske Videnskabernes Selskab, 5(4), 1-34 (1948)] was used. When comparing two results (e.g. the arcuate by clustering vs. the arcuate by expert drawing), the SD index is calculated by $2c/(n\_1+n\_2)$, where c is the overlapping tract volume (number of voxels) covered by both results and $n\_1$, $n\_2$ are the volumes for individual results. The SD index takes values in the interval [0,1], where 1 means a complete agreement. For the cingulum bundle, the average agreement between the clustering approach and experts was 0.81 while the average agreement between the experts was 0.89. Both agreement levels decrease significantly for the arcuate as seen in FIG. 10, with a SD index of 0.62 between the clustering approach and experts and 0.73 between the experts. The reproducibility of the expert results was quantified by calculating the SD index for their repeated drawings. The same cingulum bundle (single subject, single time point) was drawn three times separated by 1-2 days. For the first expert, the average SD index was 0.93, and 0.85 for the second one, yielding an average SD index of 0.89. This gives an intuition of the limits on the reproducibility of a single tract when drawn by experts repeatedly. When using Adaptive Clustering on the same fiber set repeatedly, the SD index is necessarily 1 (ignoring the slight variations caused by the EM algorithm). Together with the fact that the results that are provided by the proposed framework are reliable enough to perform a population study, the proposed framework can ably assist experts in the clinical studies.

Example 2

Automated Identification of Fiber Pathways in Patients with Edema and Tumor Mass A. Tensor Model and Tractography Quality assurance of the acquired data was conducted to detect artifacts and outliers, followed by diffusion weighted imaging (DWI) de-noising using Slicer [Pieper, S., et al, (2004) 3D Slicer. In: IEEE International Symposium on Biomedical Imaging; p. 632-635] and brain extraction using FSL [M. Jenkinson, et al. (2012) Neuroimage, 62(2): 782-790]. Tensors were fitted to the DWI data using multivariate linear fitting [C. Pierpaoli and Basser P J, (1996), Magn Reson Med, 36(6); 893-906] by in-house software. The WM fiber pathways were generated by the standard DTI tractography method (FACT) as implemented by TrackVis [Wang R., et al. (2007) Diffusion Toolkit: A Software Package for Diffusion Imaging Data Processing and Tractography. In Intl Soc Mag Reson Med; 3720], with default parameters and by seeding from the entire WM region. In order to calculate the connectivity profiles of fibers, the probtrackx utility of the FSL software [Jenkinson (2012) cited above] was used, again with default parameters.

The present process utilizes two extra steps for each participant, compared to the standard clinical use of DTI, namely connectivity analysis and identification of the WM tracts. The automated identification of the entire set of WM tracts takes only a few minutes to run on a personal computer (PC).

B. Methodological Details

Here, the proposed tract extraction framework is presented by first describing the representation of fibers. Then, how a fiber bundle atlas can be constructed based on the Mixture of Multinomials (MMN) clustering model is demonstrated. Finally, an adaptive MMN is introduced which incorporates the generated atlas as a prior for the clustering of a new subject, so as to automatically establish correspondence between bundles of different subjects.

A similar approach was proposed before for healthy cases (Example 1), using the Mixture of Gaussians Model (MGM) [Tunc, et al, Lecture Notes in Computer Science, 2013: 730-741]. The main technical difference between this example and the preceding Example is the way fiber bundles are represented in the model. Previously, fiber bundles were represented by Gaussian distributions, each parameterized by a mean vector and covariance matrix. MGM model poses several difficulties when the variation of bundles increases due to the distortion of white matter fibers by edema and mass effect. Specifically, the possible singularity of the covariance matrix due to high dimensionality (95 in our case) hinders a successful atlas generation, and thereby automated extraction of bundles in a test subject. Thus, here a more stable model based on MMN is implemented that is not affected by dimensionality, unlike MGM. In MMN, each fiber bundle is represented by a multinomial distribution, encoding the probabilities that fibers tend to connect gray matter regions. This model was performed as described earlier in this specification.

Example 3

Automated Identification of Fiber Pathways: Novel Paradigm for Neurosurgical Planning and Resection of Gliomas An automated tract identification paradigm was developed and assessed for reliability in the resection of human gliomas and general neurosurgical use. A fiber bundle atlas was generated from six healthy participants. Fibers of a test set (including three healthy participants and ten patients with brain tumors) were clustered adaptively using this atlas. Reliability of identified tracts in both groups was assessed by comparison with two experts, using Cohen's kappa to quantify concurrence.

The automated paradigm demonstrated a reliable and practical method to identify white mater tracts, even when in the presence of mass effect, edema, and tract infiltration. When the tumor demonstrated significant mass effect or shift, the automated approach was useful to provide an initialization to guide the expert to identify the specific tract of interest.

Thus, this study shows a reliable paradigm for automated identification of white matter pathways in patients with gliomas. This approach could not only enhance safety, but also could be used for longitudinal studies to assess the integrity of key fiber tracts.

Methods

Participants

The tract identification paradigm was assessed on two datasets comprised of healthy participants and tumor patients. The first dataset consisted of nine healthy participants (six males and three females, age 31.25±4.2 years) imaged at three time points separated by two weeks. This dataset was used to confirm the accuracy and reproducibility of the algorithm in healthy controls, and served as the basis to create the atlas of fiber bundles. Six male participants were selected to generate the fiber bundle atlas, and remaining three participants were used in testing. The second dataset consisted of 10 male patients (age 57.3±18.3 years) with gliomas (astrocytomas and oligodendrogliomas) of various histological grades.

MRI Acquisition

Data of healthy participants was acquired on a Siemens 3T Verio™ with a monopolar Stejskal-Tanner diffusion weighted spin-echo, echo-planar imaging sequence (TR/TE=14.8s/11 ms, 2 mm isotropic voxels, b=1000 s/mm$^2$ and 64 gradient directions). Data of the patients with gliomas were acquired using Siemens 3T TrioTim scanner, echo-planar imaging sequence (TR/TE=5s/86 ms, 1.7×1.7×3 mm anisotropic voxels, b=1000 s/mm$^2$, 30 gradient directions).

Automated Identification of Tracts

The process described herein utilizes a fiber bundle atlas that will emulate the expert, as the bundles will be annotated by experts. The white matter tracts in any subject with a brain tumor are then extracted based on the definitions encoded in the atlas. In order to build an atlas, a connectivity-based representation of white matter fibers was created. To achieve this, the brain was first parcellated into 95 regions by mapping the Desikan atlas [Neuroimage, 2006; 31(2)] to each brain. For healthy subjects, FreeSurfer was for the parcellation as described in Example 1, whereas DRAMMS: Deformable registration via attribute matching and mutal-saliency weighting [Ou Y, et al (2011) Med Image Anal. 15(4): 622-639] was used with patients due to its robustness to deformations induced by tumors. Whole brain fibers were generated using TrackVis (as described in Example 2), and each voxel of a fiber was represented by a 95-dimensional vector encoding the connection probabilities to the 95 regions, generated using the probabilistic tractography tool probtrackx. Finally, a fiber was represented by the average of these vectors for all of its voxels, termed the connectivity profile of the fiber. The connectivity based representation of fibers is expected to be robust to minor changes in the parcellation of the cortex; therefore, possible shortcomings of the registration with patients is not supposed to effect the final tract extraction results critically.

Figure 11:
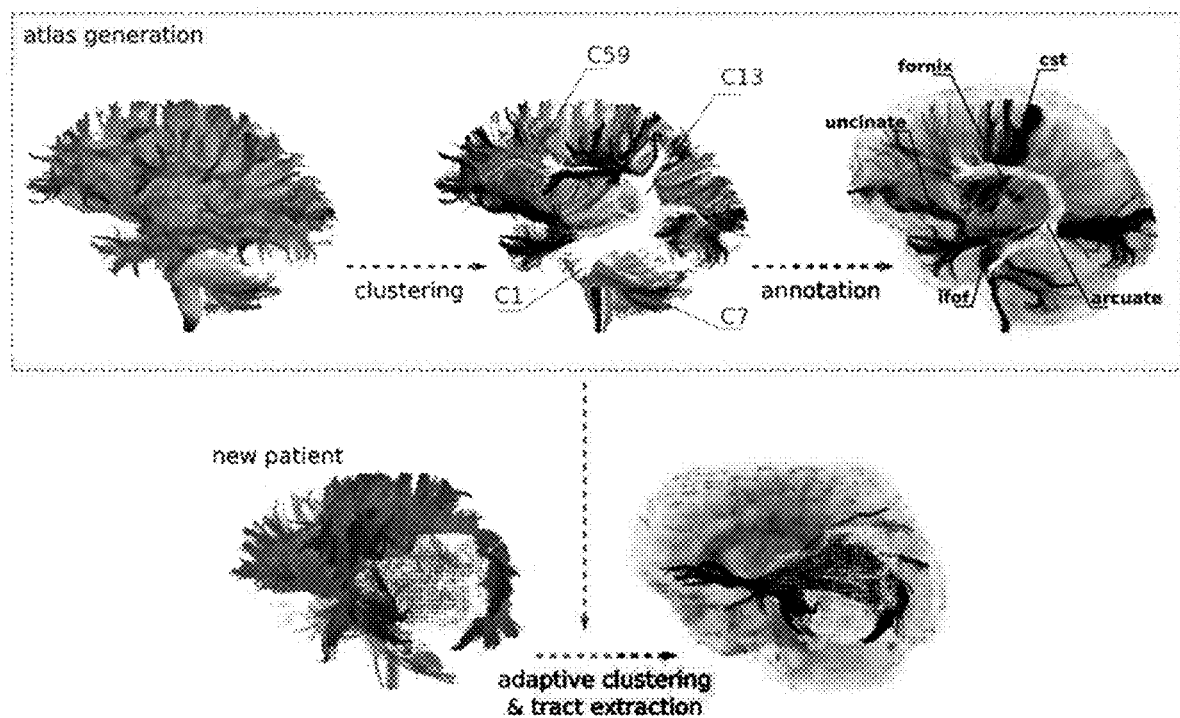
FIG. 11 illustrates the steps of automated tract identification. The WM fiber bundle atlas is generated by clustering several atlas subjects. Atlas is then annotated according to the WM tracts that fiber bundles belong to. Fibers of a new subject are clustered adaptively by employing the atlas as a prior model. This procedure results in automated correspondence across fiber bundles of different subjects that are adapted to the same atlas.

As described in Example 1, six healthy participants were selected to generate a fiber bundle atlas. Whole brain fibers of all were clustered based on their connectivity profiles. All fiber bundles in the atlas were annotated by an expert to identify the WM structures that they belong to. This atlas, which establishes automated correspondence between participants, was then used as a prior model for clustering remaining participants (patients and healthy controls) in a fully automated manner (FIG. 11). The modified clustering algorithm provides increased accuracy and stability associated with the distortion of WM fibers by edema and mass effect.

Evaluation of Automated Tract Identification

The automated tract identification results were evaluated via a comparison with those obtained from two experts by manual placement of ROIs. These experts identified six white matter tracts, selected for proximity to the lesion, favoring tracts that were pathologically affected and displaced. Both experts repeated the drawing of ROIs three times, separated by at least a day to estimate the intra-observer reproducibility. Agreements were quantified using Cohen's kappa. Cohen's kappa takes values in the interval (0,1), where higher values indicate a better agreement. A kappa value of 0.41-0.60 is considered as moderate agreement while 0.61-0.80 as substantial and 0.81-1.0 as almost perfect agreement. Voineskos, et al, Neuroimage, 2009; 45(2): 370-376]. Furthermore, the selected tracts were compared in terms of a scalar index derived from the diffusion tensor, namely fractional anisotropy.

Results

First, the reliability of the framework is assessed by quantitative empirical results based on comparisons of automatically identified white matter tracts to those identified with expert drawings. Then, the applicability of the process of the invention to surgical planning was demonstrated.

Reliability of Tract Identification

Figure 12A:
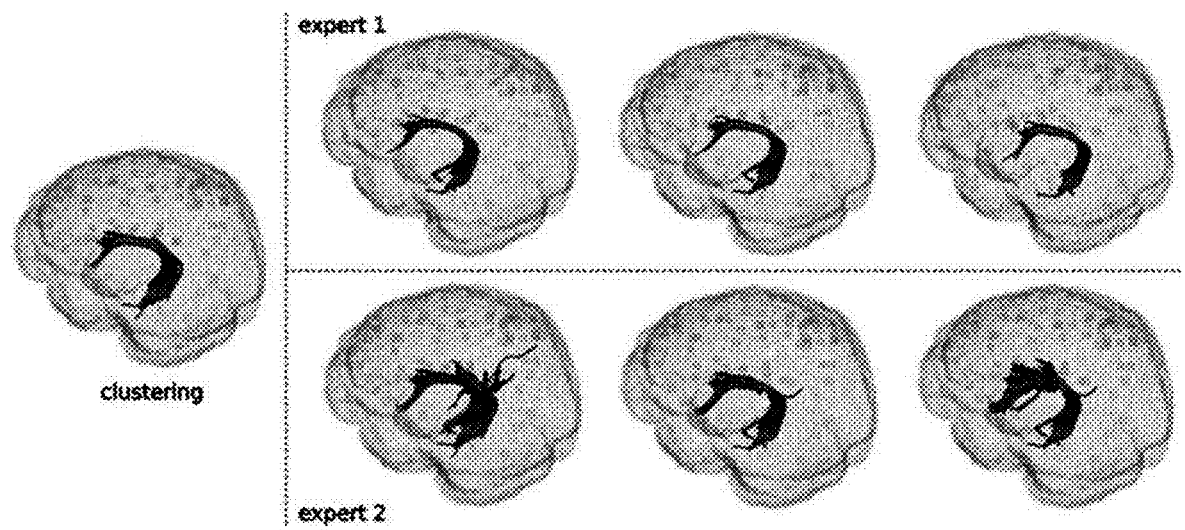
FIGS. 12A and 12B provide a comparison of the clustering results for the AF and IFOF to expert drawings for two healthy subjects. Each expert repeated the drawing three times (columns) separated by at least a day. The high variation between expert drawings is evident. Overall agreement between the clustering results and the experts suggests a high reliability of the clustering paradigm.
Figure 12B:
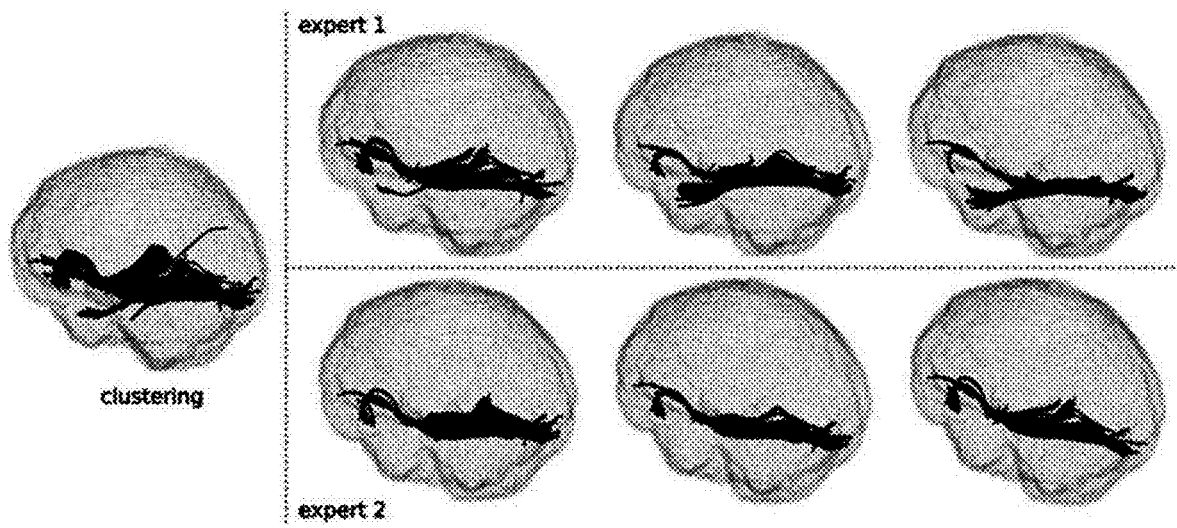

In order to validate the proposed methodology, the automatically identified white matter tracts was evaluated in healthy participants. For example, the inferior fronto-occipital fasciculus (IFOF) and the arcuate fasciculus (AF) were assessed and then compared the results to those that were produced by experts using manual ROIs (FIG. 12). A summary of quantified comparisons for healthy participants is found in the following Table 2.

Table 2: Agreement between clustering and experts as quantified by Cohen's kappa for healthy controls and patients with brain tumors. Six tracts, namely the arcuate fasciculus (AF), the inferior fronto-occipital fasciculus (IFOF), the inferior longitudinal fasciculus (ILF), the cingulum bundle (CB), the fornix (FR), and the uncinate fasciculus (UF) were identified. Mean and standard deviation (in parentheses) are given. C: clustering, $E_1$: expert 1, $E_2$: expert 2, E: both experts (average of both). Intra-expert agreement quantifies the variation with the repeated drawings. The overall agreement between clustering and experts (C vs. E) is comparable to the agreement between experts ($E_1$ vs. $E_2$).

TABLE 2

| Bundle | Healthy Controls | | | Patients | |
|---|---|---|---|---|---|
| | C vs. E | $E_1$ vs. $E_2$ | E (Intra) | C vs. E | $E_1$ vs. $E_2$ |
| IFOF | 0.66 (0.05) | 0.61 (0.08) | 0.61 (0.14) | 0.49 (0.21) | 0.42 (0.22) |
| ILF | 0.62 (0.09) | 0.67 (0.04) | 0.69 (0.10) | 0.59 (0.17) | 0.55 (0.20) |
| AF | 0.64 (0.10) | 0.46 (0.16) | 0.78 (0.18) | 0.46 (0.21) | 0.49 (0.19) |
| UF | 0.60 (0.13) | 0.89 (0.03) | 0.91 (0.05) | N/A | |
| CB | 0.76 (0.05) | 0.74 (0.05) | 0.89 (0.04) | | |
| FR | 0.61 (0.07) | 0.59 (0.04) | 0.83 (0.12) | | |

The variation in expert drawings, both for inter- and intra-user measures, are conspicuously high (Table 2), illustrating the difficulty for an expert to draw ROIs reproducibly, even in healthy participants. A detailed set of comparisons is provided as follows:

TABLE 3

Mean percent differences in FA values for healthy controls. The standard deviations are given in parentheses. C: clustering, $E_1$: expert 1, $E_2$: expert 2, E: both experts (average of both). Intra-expert agreements quantify the difference between the repeated drawings. The overall difference between clustering and experts (C vs. E) is comparable to the difference between experts ($E_1$ vs. $E_2$).

| Table 3. Bundle | C vs. $E_1$ | C vs. $E_2$ | C vs. E | $E_1$ vs. $E_2$ | $E_1$ (Intra) | $E_2$ (Intra) | E (Intra) |
|---|---|---|---|---|---|---|---|
| IFOF | 3.26 (0.70) | 3.90 (1.11) | 3.58 (0.98) | 5.16 (1.18) | 4.65 (1.03) | 7.32 (1.47) | 5.98 (1.84) |
| ILF | 2.58 (1.68) | 1.50 (0.36) | 2.04 (1.33) | 2.70 (0.82) | 1.89 (0.28) | 2.36 (0.31) | 2.12 (0.38) |
| AF | 3.58 (1.63) | 1.95 (0.82) | 2.76 (1.53) | 4.28 (2.30) | 0.80 (0.30) | 1.17 (0.37) | 0.98 (0.39) |
| UF | 3.46 (2.47) | 2.51 (1.66) | 2.98 (2.16) | 2.00 (1.30) | 1.17 (1.06) | 2.03 (1.17) | 1.60 (1.20) |
| CB | 1.16 (0.30) | 1.41 (0.58) | 1.29 (0.48) | 0.64 (0.14) | 1.00 (0.14) | 0.33 (0.06) | 0.66 (0.35) |
| FR | 1.67 (0.44) | 1.25 (0.68) | 1.46 (0.61) | 2.39 (0.17) | 1.76 (1.60) | 1.47 (1.54) | 1.62 (1.58) |

Table 4: Agreement between clustering and experts as quantified by Cohen's kappa for patients with brain tumors. The standard deviations are given in parentheses. C: clustering, $E_1$: expert 1, $E_2$: expert 2, E: both experts (average of both). Intra-expert agreement quantifies the variation with the repeated drawings. The overall agreement between clustering and experts (C vs. E) is generally higher than the agreement between experts ($E_1$ vs. $E_2$).

TABLE 4

| Bundle | C vs. $E_1$ | C vs. $E_2$ | C vs. E | $E_1$ vs. $E_2$ |
|---|---|---|---|---|
| IFOF | 0.58 (0.22) | 0.40 (0.16) | 0.49 (0.21) | 0.42 (0.22) |
| ILF | 0.58 (0.22) | 0.60 (0.08) | 0.59 (0.17) | 0.55 (0.20) |
| AF | 0.37 (0.18) | 0.56 (0.18) | 0.46 (0.21) | 0.49 (0.19) |

Table 5: Mean percent differences in FA values for patients with brain tumors. The standard deviations are given in parentheses. C: clustering, $E_1$: expert 1, $E_2$: expert 2, E: both experts (average of both). Intra-expert agreements quantify the difference between the repeated drawings. The overall difference between clustering and experts (C vs. E) is less than the difference between experts ($E_1$ vs. $E_2$).

TABLE 5

| Bundle | C vs. $E_1$ | C vs. $E_2$ | C vs. E | $E_1$ vs. $E_2$ |
|---|---|---|---|---|
| IFOF | 4.19 (4.60) | 7.95 (4.20) | 6.07 (4.79) | 8.37 (8.15) |
| ILF | 5.47 (5.95) | 3.26 (1.82) | 4.36 (4.54) | 6.80 (5.90) |
| AF | 7.01 (4.78) | 4.52 (2.23) | 5.85 (4.01) | 6.42 (5.42) |

Figure 13A:
FIGS. 13A-13C provide a comparison of the clustering results (FIG. 13A) for the ILF (first column), IFOF (second column), and the AF (third column) with the expert drawings (FIGS. 13B and 13C) for a patient with glioma. Edema volume is depicted by the gray shade. Due to high amount of deformation induced by mass effect, drawings of experts vary significantly as they need to the find best inclusion and exclusion ROIs heuristically.
Figure 13B:
Figure 13C:

The difficulty in ROI identification is compounded in the presence of gliomas. This was demonstrated when experts placed ROIs to isolate the ILF, IFOF, and AF in patients with gliomas (FIG. 13). Quantitative comparisons (Table 2) show that our method generates reliable results in patients with gliomas. Even with extreme deformation of the white matter, as in a patient with a prior surgical resection of a tumor, the white matter fibers within the internal capsule could be reliably visualized (FIG. 14).

Automated Tract Identification in Surgical Planning

Figure 15:
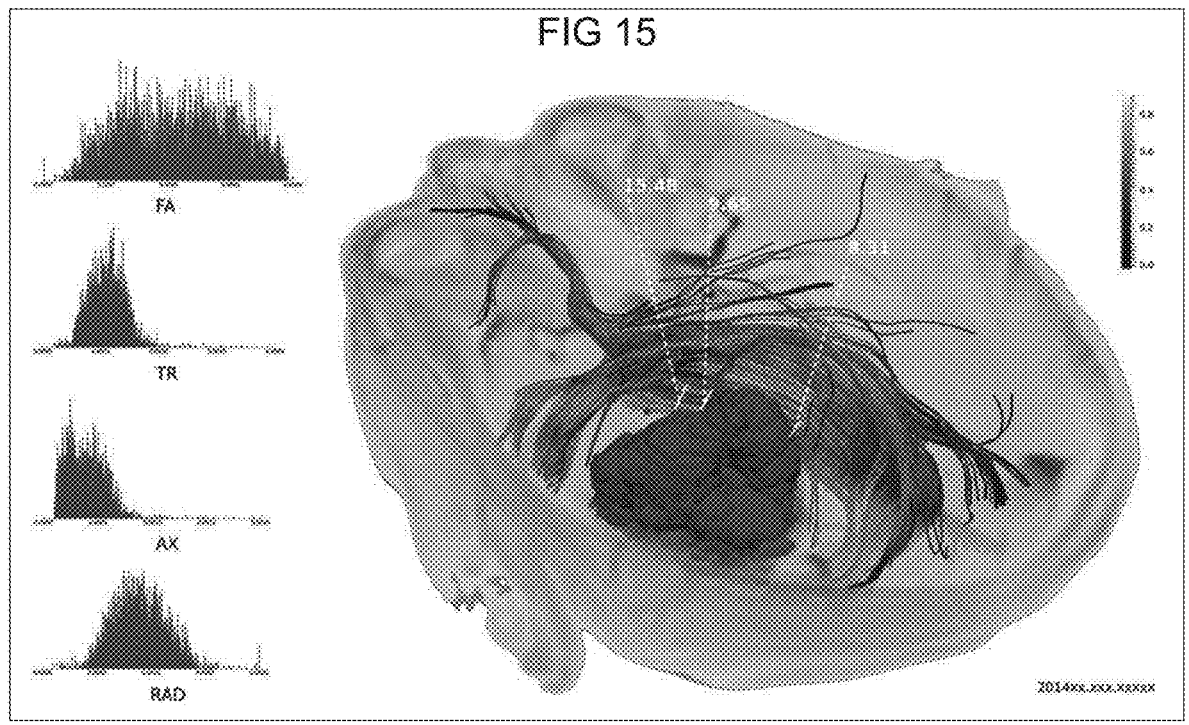
FIG. 15 illustrates a tumor (black mass) and surrounding WM tract (IFOF). The IFOF is overlaid with FA map to show how the tract is affected by the tumor. Distances between manually selected points on the tumor and the tract are shown. On the left side are distributions of several diffusion scalars along the tract.

In surgical planning, the process and apparatus described herein can improve the visualization of white matter tracts in close proximity to the lesion/surgical target. FIG. 15 demonstrates an automatically extracted IFOF, facilitating efficient visualization of this affected tract without any manual intervention. Additionally, the approach described herein enables the selection of points along this tract, to further augment surgical planning. At each point, a DTI-based scalar index can be calculated, compared to a normative range, to estimate tract integrity. Additionally, proposed resection margins can also be indicated, through individual points, and the distance to the tract from each of these points is automatically provided (FIG. 15).

Figure 16:
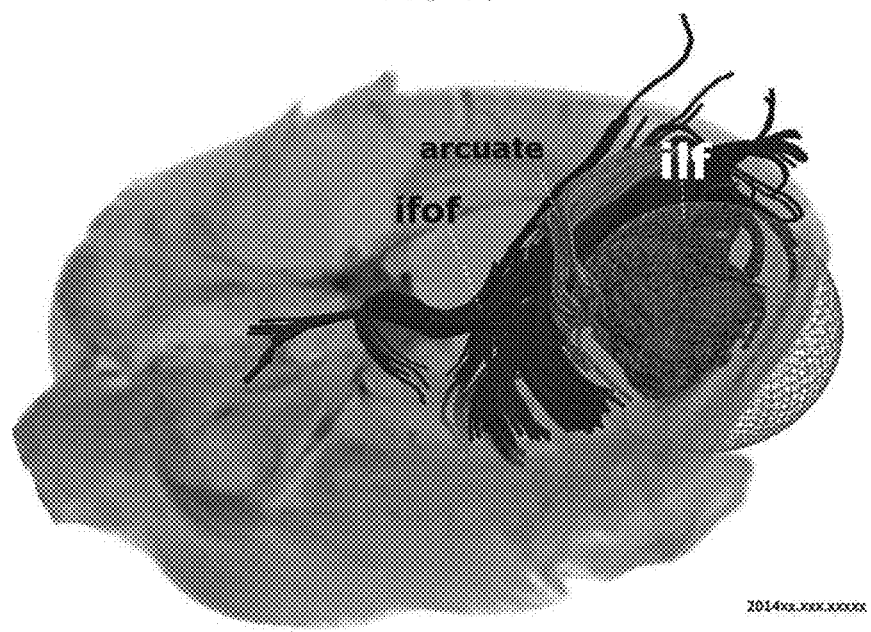
FIG. 16 illustrates a glioma (black mass) and surrounding three WM tracts, namely IFOF, ILF, and AF are illustrated. The spherical volume depicts the maximal margin of resection that is estimated so that selected WM tracts are not affected. The estimated maximal margin depends on specific WM tracts selected.
Figure 17A:
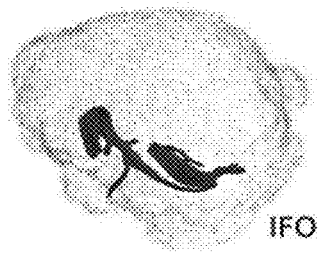
FIGS. 17A-17D illustrates a patient with large mass effect. Both FA and FLAIR slices are shown on the top panel, where the effects of the tumor and edema are evident. Clustering results for IFOF, ILF, and AF are shown in FIG. 17A, FIG. 17B, and FIG. 17C, respectively. Although tracts are only partially identified, these provide an initial estimate that was improved subsequently by experts (middle panel). Note that the partial fibers of tracts are captured successfully by the clustering algorithm.
Figure 17B:
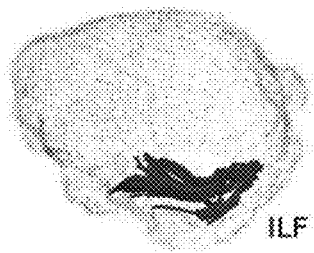
Figure 17C:
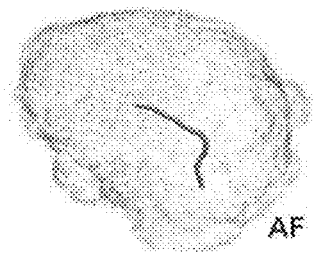
Figure 17D:
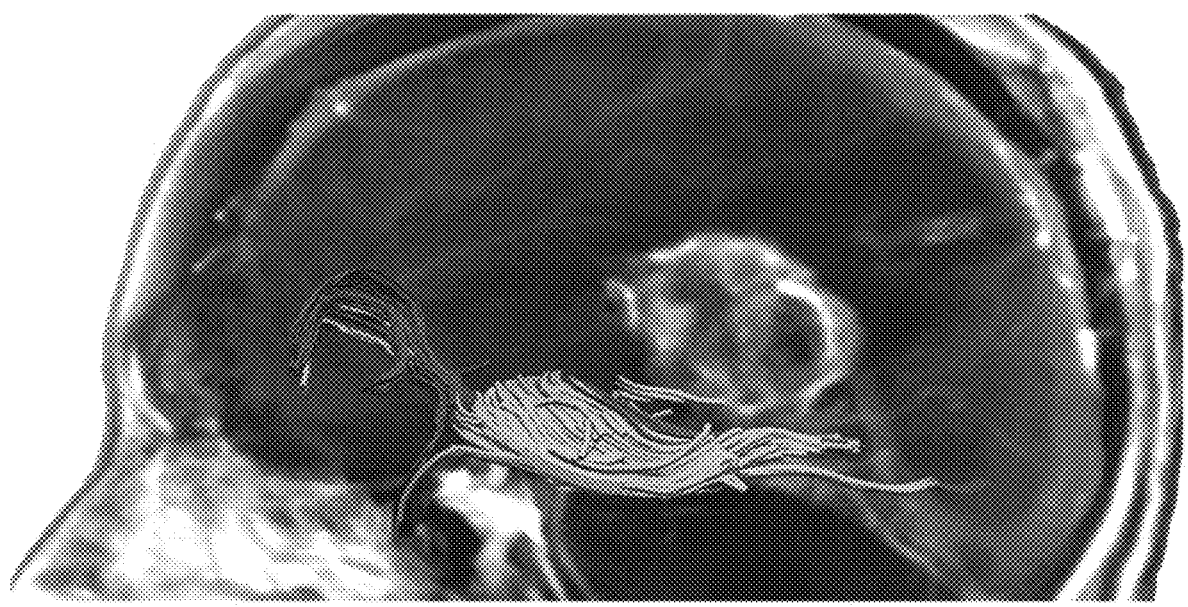

FIG. 16 shows a proposed resection plan for a patient with a glioma. This plan is likewise enhanced using automated tract identification. The tumor and three white matter tracts (IFOF, ILF, AF) in proximity to the lesion are visualized. A proposed "resection region" is subsequently calculated, representing the tumor and the surrounding margin that can be resected with minimal or no damage to the surrounding tracts.

Finally, the concept of an initialization for white matter tract identification is demonstrated in FIG. 17. In the commonly encountered situation where white matter fibers are obscured due to excessive edema, mass effect, or infiltration, our paradigm provides an initial location of the tract. This location can be subsequently refined by an expert to provide a more detailed and accurate tract representation.

DISCUSSION

Currently, white matter tract identification relies on the manual drawing of ROIs by experts. The manual placement of ROIs becomes especially challenging in the presence of human gliomas that are characterized by peritumoral vasogenic edema and mass effect. Anatomical landmarks, used by experts to identify tract location, can be obscured by these confounders. Moreover, tracts that are affected by tumor or edema can terminate prematurely during tractography. The working examples herein demonstrate that the method of the invention improves or avoids many of the limitations associated with prior art tract identification techniques. This connectivity-based fiber characterization is uniquely beneficial since fiber bundles can be identified irrespective of changing fiber shape and location, or situations where the fiber is disrupted (FIG. 13, FIG. 14, and FIG. 17). It should be noted, however, that our approach is utilized once the tractography is performed, to identify any tract of interest among the whole brain tractography results. Hence, the proposed methodology should not be taken as resolving or eliminating, to any extent, intrinsic limitations of DTI and tractography such as the ones caused by edema and infiltration. [White N S, et al, Cancer Res, 2014: 74(17): 4638-4652; Chen, Z., et al, NeuroImage Clin 2015: 7: 815-822; Lecoeur J., et al, MICCAI 2014 DTI TractographyChall (2014)]. Further, these results were produced using a simple tensor model and tractography method in order to demonstrate the potential of the invention. Thus, improved outcomes can be attained using more advanced and sophisticated image reconstruction schemes and tractography algorithms. [Tournier J-D., et al, Magn Reson Med. 2011: 65(6): 1532-1556; Farquharson, S., et al., J Neurosurg. (2013); 118(6): 1367-1377].

Neurosurgeons rely on specialized navigation software during surgery for localization and identification of critical, though often indistinct, brain structures. The methods and apparatus described herein can augment such navigation capabilities by providing white matter information in an efficient and reproducible manner that is currently unavailable (FIG. 15 and FIG. 16). Furthermore, the approach described herein goes beyond simple visualization of anatomical relationships. FIG. 15 demonstrates how the proposed methodology could inform the surgeon on the state of the surrounding white matter tissue. In FIG. 16, a safe "maximal resection" margin is estimated based on the selected white matter tracts of interest in proximity to a surgical target. Due to the speed and ease of automated identification of tracts, any number of tracts can now be visualized on the fly, without the need for a ROI-based plan. In current clinical practice, tracts required by the surgeon are mapped out in advance. By using the proposed tool, any tract can be interrogated at any time by any clinician. This is expected to provide immense flexibility for treatment planning, whether performed by radiologists, radiation oncologists, or surgeons.

With standard methods, the ROIs selected by experts can vary significantly, especially for complex tracts. [Bürgel, U., et al, Cent Eur Neurosurg. (2009): 70(1): 27-35]. The methods provided herein reliably generate reproducible white matter tracts by comparing automated results with those drawn manually by experts. The overall agreement of the results of automated clustering with the experts in healthy subjects was comparable to the agreement between experts, underscoring the reliability of automated clustering as compared to manual identification by experts. Similar results were also observed in patients with brain tumors. In expert generated tracts, the placement of ROIs was left to individual discretion, instead of defining a standard drawing protocol, to capture expert variability more realistically. Thus, the overall agreement between experts is expected to be lower than what is usually reported in studies where a standard drawing protocol is assumed for all the experts. Voineskos, A N, et al, Neuroimage, 2009; 45(2): 370-376.

In cases where fiber tractography cannot produce a complete set of fibers due to extensive edema or mass effect, our framework can be used to identify the approximate location of a given tract (FIG. 17). This provides context for the expert when placing ROIs manually. This iterative and recursive improvement approach that interweaves the automated tract identification with expert refinement is beneficial even when the tracts can be identified successfully. This can be observed in FIG. 12, FIG. 13, and FIG. 16 where part of ILF is clustered together with IFOF, due to the way the tracts are defined in the atlas. Future improvement in the atlas will be made by increasing the number of participants used in atlas generation as well as incorporating annotations by several experts.

All patents, patent publications, and other publications listed in this specification, are incorporated herein by reference. While the invention has been described with reference to a particularly preferred embodiment, it will be appreciated that modifications can be made without departing from the spirit of the invention. Such modifications are intended to fall within the scope of the appended claims.

The invention claimed is:

1. A method for processing diffusion data for identification of white matter tracts in the brain of a patient, said method comprising, with a processor:
   (a) generating a connectivity based representation of white matter fibers for multiple different subjects from the connectivity signatures of the fibers from a diffusion magnetic resonance imaging (dMRI) without using the physical coordinates of the fibers;
   (b) generating a fiber bundle atlas from the connectivity based fiber representation of (a) which define a model of the human brain;
   (c) adaptively clustering fibers of a new patient utilizing the fiber bundle atlas of (b) to extract white matter tracts; and
   (d) presenting the selected white matter tracts and diffusion data in a report or on a display device.

2. The method according to claim 1, wherein (a) further comprises constructing a connectivity based fiber representation by (i) defining a parcellation of the brain of each of the multiple different subjects into regions by mapping an anatomic atlas including these regions to each of the subjects and (ii) determining the weighted average connectivity signatures over voxels of fibers to define a compact representation of each of the fibers from the multiple different subjects.

3. The method according to claim 1, wherein (b) further comprises incrementally merging the connectivity signature of the fibers of the multiple different subjects from (a) and clusters over the combined set.

4. The method according to claim 1, further comprising labelling the resulting fiber bundles in the atlas (b) to indicate the anatomic white matter structures to which the bundles correspond.

5. The method according to claim 4, wherein the scan results of a new patient are assessed using the labelled atlas.

6. The method according to claim 5, wherein a track of interest (TOI) for a new patient is extracted from whole brain tractography results using the labelled atlas.

7. The method according to claim 1, wherein white matter tracts are identified in patients in the presence of edema, mass effect and/or tract infiltration.

8. A non-transitory computer readable medium carrying software for controlling a processor to carry out the method of claim 1.

9. A diffusion data processing apparatus for performing white matter tract-based analysis with large samples, said apparatus comprising:
   (a) a connectivity based fiber contents processor arranged to permit comparison or combination of fibers of multiple different subjects which utilizes the connectivity signatures of the fibers from a diffusion magnetic resonance imaging (dMRI) without using the physical coordinates of the fibers;
   (b) a fiber bundle apparatus processor which defines an atlas of the fiber bundles in the human brain;
   (c) a clustering processor arranged to adaptively cluster fibers of a new patient utilizing the fiber bundle atlas of (b).

10. The apparatus according to claim 9, further comprising a report generator.

11. An imaging system comprising a diffusion magnetic resonance imaging apparatus and the data processing apparatus according to claim 9.

12. A diffusion magnetic resonance imaging apparatus comprising:
   (a) a diffusion magnetic resonance imaging (dMRI) apparatus for obtaining diffusion data;
   (b) a connectivity based fiber contents processor arranged to permit comparison or combination of fibers of multiple different subjects which utilizes the connectivity signatures of the fibers from the dMRI without using the physical coordinates of the fibers;
   (c) a fiber bundle apparatus processor which defines a model of the fiber bundles in the human brain; and
   (d) a clustering processor arranged to adaptively cluster fibers of a new patient utilizing the fiber bundle atlas of (c); and
   (e) an output device which outputs or displays a report.

13. A method for designing a treatment plan for glioma patients in the optional presence of edema, mass effect and/or tract infiltration, using a processor, said method comprising:
   (a) generating a connectivity based representation of white matter fibers for multiple different subjects from the connectivity signatures of the fibers from a diffusion magnetic resonance imaging (dMRI) without using the physical coordinates of the fibers;
   (b) generating a fiber bundle atlas from the connectivity based fiber representation of (a) which define a model of the human brain;
   (c) adaptively clustering fibers of a glioma patient utilizing the fiber bundle atlas of (b); and
   (e) presenting the diffusion data in a report or on a display device.

* * * * *